(12) United States Patent
Merce Vidal et al.

(10) Patent No.: US 7,414,070 B2
(45) Date of Patent: Aug. 19, 2008

(54) INDOL-7-YL SULFONAMIDE DERIVATIVES, THEIR PREPARATION AND THEIR USE IN PHARMACEUTICAL COMPOSITIONS

(75) Inventors: Ramon Merce Vidal, Barcelona (ES); Xavier Codony Soler, Mataro (ES); Alberto Dordal Zueras, Barcelona (ES)

(73) Assignee: Laboratorios del Dr. ESTEVE S.A., Barcelona (ES)

( * ) Notice: Subject to any disclaimer, the term of this patent is extended or adjusted under 35 U.S.C. 154(b) by 0 days.

(21) Appl. No.: 10/566,403

(22) PCT Filed: Jul. 29, 2004

(86) PCT No.: PCT/ES2004/008513

§ 371 (c)(1),
(2), (4) Date: Aug. 11, 2006

(87) PCT Pub. No.: WO2005/013979

PCT Pub. Date: Feb. 17, 2005

(65) Prior Publication Data

US 2007/0185207 A1 Aug. 9, 2007

(30) Foreign Application Priority Data

Jul. 30, 2003 (ES) ................. 200301808

(51) Int. Cl.
*A01N 43/38* (2006.01)
*A61K 31/405* (2006.01)
*C07D 209/04* (2006.01)

(52) U.S. Cl. ..................... 514/415; 548/491
(58) Field of Classification Search ............. 548/491; 514/415; 546/491
See application file for complete search history.

(56) References Cited

U.S. PATENT DOCUMENTS

| | | | |
|---|---|---|---|
| 3,472,870 A | 10/1969 | Larsen et al. | |
| 6,448,243 B1 | 9/2002 | Kitazawa et al. | |
| 2003/0191124 A1 | 10/2003 | Merce-Vidal et al. | |
| 2005/0032791 A1 | 2/2005 | Merce-Vidal et al. | |
| 2005/0065202 A1 | 3/2005 | Vidal et al. | |

FOREIGN PATENT DOCUMENTS

| | | |
|---|---|---|
| EP | 0815861 | 1/1998 |
| JP | 2002167376 | 6/2002 |
| WO | 99/28297 | 6/1999 |
| WO | 02/060871 | 8/2002 |
| WO | 03/042175 | 5/2003 |

OTHER PUBLICATIONS

Meneses et al., Cellular and Molecular Neurobiology,2002, vol. 22, pp. 675-688.*
Laconde et al., Journal of enzyme inhibition and medicinal chemistry, 2003, vol. 18, pp. 89-94.*
U.S. Appl. No. 11/679,344, filed Feb. 27, 2007, Merce Vidal.
U.S. Appl. No. 11/673,328, filed Feb. 9, 2007, Merce Vidal et al.
U.S. Appl. No. 10/566,403, filed Aug. 11, 2006, Merce-Vidal et al.
Laconde, G. et al., "New analogues of the anticancer E7070: Synthesis and pharmacology", Journal of Enzyme Inhibition and Medicinal Chemistry, vol. 18, No. 2, pp. 89-94, 2003.
U.S. Appl. No. 10/566,094, filed Jan. 27, 2006, Merce Vidal et al.
U.S. Appl. No. 10/566,403, filed Jan. 30, 2006, Merce Vidal et al.
U.S. Appl. No. 10/566,101, filed Jan. 27, 2006, Merce Vidal et al.
U.S. Appl. No. 10/566,164, filed Jan. 27, 2006, Merce Vidal et al.
U.S. Appl. No. 10/566,100, filed Jan. 27, 2006, Torrens Jover et al.
U.S. Appl. No. 10/566,402, filed Jan. 30, 2006, Torrens Jover et al.

* cited by examiner

*Primary Examiner*—D. Margaret Seaman
*Assistant Examiner*—Niloofar Rahmani
(74) *Attorney, Agent, or Firm*—Oblon, Spivak, McClelland, Maier & Neustadt, P.C.

(57) ABSTRACT

The present invention refers to new sulfonamide derivatives, of general formula (Ia, Ib, Ic), optionally in form of one of their stereoisomers, preferably enantiomers or diastereomers, their racemate, or in form of a mixture of at least two of their stereoisomers, preferably enantiomers or diastereomers, in any mixing ratio, or their salts, preferably the corresponding, physiologically acceptable salts, or corresponding solvates; to the processes for their preparation, to their application as medicaments in human and/or veterinary therapeutics, and to the pharmaceutical compositions containing them.

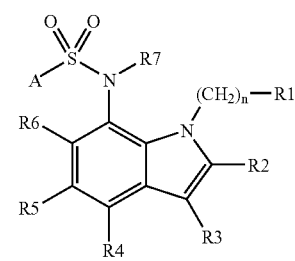

(Ia, Ib, Ic)

44 Claims, No Drawings

INDOL-7-YL SULFONAMIDE DERIVATIVES, THEIR PREPARATION AND THEIR USE IN PHARMACEUTICAL COMPOSITIONS

The present invention refers to new sulfonamide derivatives, of general formula (Ia, Ib, Ic),

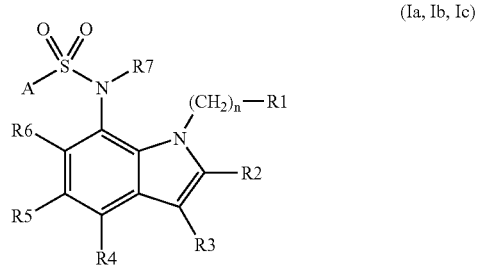

(Ia, Ib, Ic)

optionally in form of one of their stereoisomers, preferably enantiomers or diastereomers, their racemate, or in form of a mixture of at least two of their stereoisomers, preferably enantiomers or diastereomers, in any mixing ratio, or their salts, preferably the corresponding, physiologically acceptable salts, or corresponding solvates; to the processes for their preparation, to their application in medicaments in human and/or veterinary therapeutics, and to the pharmaceutical compositions containing them.

The new compounds of the present invention may be used in the pharmaceutical industry as intermediates and for preparing medicaments.

The superfamily of serotonin receptors (5-HT) comprises 7 classes ($5\text{-}HT_1\text{-}5\text{-}HT_7$), which cover 14 human subclasses [D. Hoyer, et al., *Neuropharmacology*, 1997, 36, 419]. The $5\text{-}HT_6$ receptor has been the last serotonin receptor identified by molecular cloning in rats [F. J. Monsma, et al., *Mol. Pharmacol.*, 1993, 43, 320; M. Ruat, et al., *Biochem. Biophys. Res. Commun.*, 1993, 193, 268] as well as in humans [R. Kohen, et al., *J. Neurochem.*, 1996, 66, 47]. The compounds with an affinity for the $5\text{-}HT_6$ receptor are useful in treating different disorders of the Central Nervous System and of the Gastrointestinal system, as well as the irritable bowel syndrome. The compounds with an affinity for the $5\text{-}HT_6$ receptor are useful for treating anxiety, depression and cognitive memory disorders [M. Yoshioka, et al., *Ann. NY Acad. Sci.*, 1998, 861, 244; A. Bourson, et al., *Br. J. Pharmacol.*, 1998, 125, 1562; D. C. Rogers, et al., *Br. J. Pharmacol. Suppl.*, 1999, 127, 22P; A. Bourson, et al., *J. Pharmacol. Exp. Ther.*, 1995, 274, 173; A. J. Sleight, et al., *Behav. Brain Res.*, 1996, 73, 245; T. A. Branchek, et al., *Annu. Rev. Pharmacol. Toxicol.*, 2000, 40, 319; C. Routledge, et al., *Br. J. Pharmacol.*, 2000, 130, 1606]. It has been shown that the typical and atypical antipsychotics for treating schizophrenia have a high affinity for the $5\text{-}HT_6$ receptors [B. L. Roth, et al., *J. Pharmacol. Exp. Ther.*, 1994, 268, 1403; C. E. Glatt, et al., *Mol. Med.*, 1995, 1, 398; F. J. Mosma, et al., *Mol. Pharmacol.*, 1993, 43, 320; T. Shinkai, et al, *Am. J. Med. Genet.*, 1999, 88, 120]. The compounds with an affinity for the $5\text{-}HT_6$ receptor are useful for treating infantile hyperkinesia (ADHD, attention deficit/hyperactivity disorder) [W. D. Hirst, et al., *Br. J. Pharmacol.*, 2000, 130, 1597; C. Gérard, et al., *Brain Research*, 1997, 746, 207; M. R. Pranzatelli, *Drugs of Today*, 1997, 33, 379].

Patent application WO 01/32646 discloses sulfonamides derived from bicycles, whereby each of the rings is 6-membered, aromatic or heteroaromatic rings with $5\text{-}HT_6$ receptor antagonist activity.

Patent application EP 0 733 628 discloses sulfonamides derived from indole with $5\text{-}HT_{1F}$ receptor antagonist activity, useful for the treatment of migraines.

Furthermore, it has been shown that the $5\text{-}HT_6$ receptor plays a role in the ingestion of food [*Neuropharmacology*, 41, 2001, 210-219].

Eating disorders, particularly obesity, are a serious and increasingly frequent threat for the health of humans from all age groups, since they increase the risk of developing other serious and even mortal diseases, preferably diabetes and coronary artery diseases.

Therefore, an object of the present invention was to provide new compounds, particularly suitable as active substances in medicaments, preferably in medicaments for $5\text{-}HT_6$ receptor regulation, for the prophylaxis and/or treatment of a disorder or disease related to food intake, preferably for the regulation of appetite, for the maintenance, increase or reduction of body weight, for the prophylaxis and/or treatment of obesity, bulimia, anorexia, cachexia or type II diabetes (non insulin dependent diabetes mellitus), preferably type II diabetes caused by obesity, for the prophylaxis and/or treatment of gastrointestinal tract disorders, preferably irritable bowel syndrome, for cognitive enhancement, for the prophylaxis and/or treatment of disorders of the central nervous system, anxiety, panic disorders, depression, preferably bipolar disorders, cognitive memory disorders, senile dementia processes, neurodegenerative disorders, preferably Alzheimer's disease, Parkinson's disease, Huntington's disease and/or Multiple Sclerosis, schizophrenia, psychosis or infantile hyperkinesia (ADHD, attention deficit/hyperactivity disorder) and other disorders mediated by the $5\text{-}HT_6$ serotonin receptor in humans and/or in animals, preferably in mammals, more preferably in humans.

It has been found that the indol-7-yl sulfonamide compounds of general formulas (Ia, Ib, Ic) described below show an affinity for the $5\text{-}HT_6$ receptor.

These compounds are therefore suitable for preparing a medicament for the prophylaxis and/or treatment of a disorder or disease related to food intake, preferably for the regulation of appetite, for the maintenance, increase or reduction of body weight, for the prophylaxis and/or treatment of obesity, bulimia, anorexia, cachexia or type II diabetes (non insulin dependent diabetes mellitus), preferably type II diabetes caused by obesity, for the prophylaxis and/or treatment of gastrointestinal tract disorders, preferably irritable bowel syndrome, for cognitive enhancement, for the prophylaxis and/or treatment of disorders of the central nervous system, anxiety, panic disorders, depression, preferably bipolar disorders, cognitive memory disorders, senile dementia processes, neurodegenerative disorders, preferably Alzheimer's disease, Parkinson's disease, Huntington's disease and/or Multiple Sclerosis, schizophrenia, psychosis or infantile hyperkinesia (ADHD, attention deficit/hyperactivity disorder) and other disorders mediated by the $5\text{-}HT_6$ serotonin receptor in humans and/or in animals, preferably in mammals, more preferably in humans. The compounds are also particularly suitable for the preparation of a medicament for cognitive enhancement.

Thus, one aspect of the present invention are compounds of general formula (Ia),

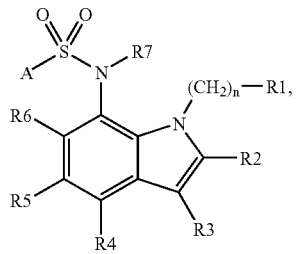

(Ia)

wherein

R$^1$ is a —NR$^8$R$^9$ radical or a saturated or unsaturated, optionally at least mono-substituted cycloaliphatic radical, which may optionally contain at least one heteroatom as a ring member and which may be condensed with a saturated or unsaturated, optionally at least mono-substituted mono- or bicyclic cycloaliphatic ring system which may optionally contain at least one heteroatom as a ring member, R$^2$, R$^3$, R$^4$, R$^5$ and R$^6$, identical or different, each represent hydrogen, halogen, nitro, alkoxy, cyano, a saturated or unsaturated, linear or branched, optionally at least mono-substituted aliphatic radical, or an optionally at least mono-substituted phenyl radical or an optionally at least mono-substituted heteroaryl radical, R$^7$ represents hydrogen or a saturated or unsaturated, linear or branched, optionally at least mono-substituted aliphatic radical, R$^8$ and R$^9$, identical or different, represent hydrogen or a saturated or unsaturated, linear or branched, optionally at least mono-substituted aliphatic radical, with the proviso that R$^8$ and R$^9$ are not hydrogen at the same time, and if one of them, R$^8$ or R$^9$, is a saturated or unsaturated, linear or branched, optionally at least mono-substituted C$_1$-C$_4$ aliphatic radical, the other one is a saturated or unsaturated, linear or branched, optionally at least mono-substituted aliphatic radical with at least five carbon atoms, or R$^8$ and R$^9$ together with the bridging nitrogen atom form a saturated or unsaturated, optionally at least mono-substituted heterocyclic ring, which may contain at least one additional heteroatom as a ring member and/or which may be condensed with a saturated or unsaturated, optionally at least mono-substituted mono- or bicyclic cycloaliphatic ring system, which may optionally contain at least one heteroatom as a ring member, A represents an optionally at least mono-substituted mono- or polycyclic aromatic ring system, which may be bonded via an optionally at least mono-substituted alkylene, alkenylene or alkynylene group and/or which may contain at least one heteroatom as a ring member in one or more of its rings, n is 0, 1, 2, 3 or 4;

optionally in form of one of its stereoisomers, preferably enantiomers or diastereomers, its racemate or in form of a mixture of at least two of its stereoisomers, preferably enantiomers or diastereomers, in any mixing ratio, or a salt thereof, preferably a corresponding, physiologically acceptable salt thereof, or a corresponding solvate thereof.

Another aspect of the present invention are compounds of general formula (Ib)

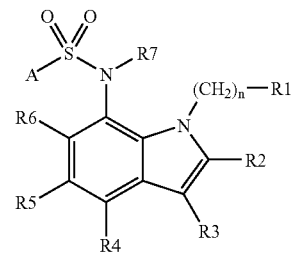

(Ib)

wherein

R$^1$ represents a —NR$^8$R$^9$ radical,

R$^2$, R$^3$, R$^4$, R$^5$ and R$^6$, identical or different, each represent hydrogen, halogen, nitro, alkoxy, cyano, a saturated or unsaturated, linear or branched, optionally at least mono-substituted aliphatic radical, or an optionally at least mono-substituted phenyl radical or an optionally at least mono-substituted heteroaryl radical, R$^7$ represents hydrogen or a saturated or unsaturated, linear or branched, optionally at least mono-substituted aliphatic radical, R$^8$ and R$^9$, identical or different, represent hydrogen or a saturated or unsaturated, linear or branched, optionally at least mono-substituted aliphatic C$_{1-4}$ radical, A represents an optionally at least mono-substituted mono- or polycyclic aromatic ring system, which may be bonded via an optionally at least mono-substituted alkylene, alkenylene or alkynylene group and/or which may contain at least one heteroatom as a ring member in one or more of its rings, n is 0, 1, 2, 3 or 4;

optionally in form of one of its stereoisomers, preferably enantiomers or diastereomers, its racemate or in form of a mixture of at least two of its stereoisomers, preferably enantiomers or diastereomers, in any mixing ratio, or a salt thereof, preferably a corresponding, physiologically acceptable salt thereof, or a corresponding solvate thereof.

Yet, another aspect of the present invention are compounds of general formula (Ic),

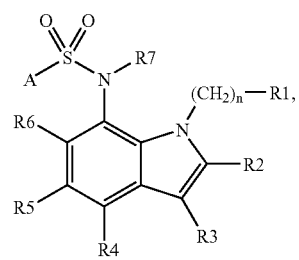

(Ic)

wherein

R$^1$ is a —NR$^8$R$^9$ radical or a saturated or unsaturated, optionally at least mono-substituted cycloaliphatic radical, which may optionally contain at least one heteroatom as a ring member and which may be condensed with a saturated or unsaturated, optionally at least mono-substituted mono- or bicyclic cycloaliphatic ring system which may optionally contain at least one heteroatom as a ring member, $R^2$, $R^3$, $R^4$, $R^5$ and $R^6$, identical or different, each represent hydrogen, halogen, nitro, alkoxy, cyano, a saturated or unsaturated, linear or branched, optionally at least mono-substituted aliphatic radical, or an optionally at least mono-substituted phenyl radical or an optionally at least mono-substituted heteroaryl radical, $R^7$ represents hydrogen or a saturated or unsaturated, linear or branched, optionally at least mono-substituted aliphatic radical, $R^8$ and $R^9$, identical or different, represent hydrogen or a saturated or unsaturated, linear or branched, optionally at least mono-substituted aliphatic radical, or $R^8$ and $R^9$ together with the bridging nitrogen atom form a saturated or unsaturated, optionally at least mono-substituted heterocyclic ring, which may contain at least one additional heteroatom as a ring member and/or which may be condensed with a saturated or unsaturated, optionally at least mono-substituted mono- or bicyclic cycloaliphatic ring system, which may optionally contain at least one heteroatom as a ring member, A represents an optionally at least mono-substituted mono- or polycyclic aromatic ring system, which may be bonded via an optionally at least mono-substituted alkylene, alkenylene or alkynylene group and/or which may contain at least one heteroatom as a ring member in one or more of its rings, n is 0, 1, 2, 3 or 4;

optionally in form of one of its stereoisomers, preferably enantiomers or diastereomers, its racemate or in form of a mixture of at least two of its stereoisomers, preferably enantiomers or diastereomers, in any mixing ratio, or a salt thereof, preferably a corresponding, physiologically acceptable salt thereof, or a corresponding solvate thereof.

If one or more of the moieties $R^2$ to $R^9$ represents a saturated or unsaturated aliphatic radical, that is, an alkyl, alkenyl or alkynyl radical, which is substituted by one or more substituents, each one of these substituents can preferably be chosen, unless otherwise defined, from the group consisting of hydroxy, fluorine, chlorine, bromine and trifluoromethyl.

If $R^1$ is a saturated or unsaturated, optionally at least one heteroatom as a ring member containing cycloaliphatic radical, which is substituted by one or more substituents and/or is condensed with a saturated or unsaturated, optionally at least mono-substituted, optionally at least one heteroatom as a ring member containing mono- or bicyclic cycloaliphatic ring system, each of these substituents can, unless otherwise defined, preferably be chosen from the group consisting of hydroxy, fluorine, chlorine, bromine, linear or branched $C_1$-$C_6$ alkyl, linear or branched $C_1$-$C_6$ alkoxy, linear or branched $C_1$-$C_6$ perfluoroalkyl, linear or branched $C_1$-$C_6$ perfluoroalkoxy and benzyl, more preferably chosen from the group consisting of linear or branched $C_1$-$C_6$ alkyl and benzyl.

The heteroatoms of said cycloaliphatic radical and/or of the mono- or bicyclic cycloaliphatic ring can, independently from one another, be chosen preferably from the group consisting of nitrogen, sulphur and oxygen, more preferably nitrogen is chosen as a heteroatom.

Said cycloaliphatic radical may contain 0, 1, 2 or 3 heteroatoms chosen from the above mentioned group, preferably it contains 0, 1 or 2 heteroatoms chosen from the above mentioned group.

If $R^8$ and $R^9$ together with the bridging nitrogen atom form a saturated or unsaturated, optionally at least mono-substituted heterocyclic ring, which may contain at least one further heteroatom as a ring member and/or which may be condensed with a saturated or unsaturated, optionally at least mono-substituted, optionally one heteroatom as a ring member containing mono- or bicyclic ring system, each one of these substituents can, unless otherwise defined, preferably be chosen from the group consisting of hydroxy, fluorine, chlorine, bromine, linear or branched $C_1$-$C_6$ alkyl, linear or branched $C_1$-$C_6$ alkoxy, linear or branched $C_1$-$C_6$ perfluoroalkyl, linear or branched $C_1$-$C_6$ perfluoroalkoxy and benzyl, more preferably from the group consisting of linear or branched $C_1$-$C_6$ alkyl and benzyl.

If the heterocyclic ring contains one or more additional heteroatoms, and/or if one or both mono- or bicyclic rings contain one or more additional heteroatoms, these heteroatoms can, independently from one another, preferably be chosen from the group consisting of nitrogen, sulphur and oxygen, more preferably nitrogen is chosen as a heteroatom.

Said heterocyclic ring may contain 0, 1, 2 or 3 additional heteroatoms chosen from the above mentioned group, preferably it contains 0 or 1 heteroatoms chosen from the above mentioned group.

If A is an optionally at least mono-substituted, optionally at least one heteroatom as a ring member containing mono- or polycyclic aromatic ring system, which can be bonded via an alkylene, alkenylene or alkynylene group, each of these substituents can preferably be chosen, unless otherwise defined, from the group consisting of hydroxy, halogen, linear or branched $C_1$-$C_6$ alkyl, linear or branched $C_1$-$C_6$ alkoxy, linear or branched $C_1$-$C_6$ perfluoroalkyl, linear or branched $C_1$-$C_6$ perfluoroalkoxy, an optionally at least mono-substituted phenyl, —O-phenyl and 5- to 6-membered heteroaryl, more preferably from the group consisting of halogen, linear or branched $C_1$-$C_6$ alkyl, optionally at least mono-substituted phenyl, —O-phenyl and 5- to 6-membered heteroaryl, even more preferably from the group consisting of fluorine, chlorine, linear or branched $C_1$-$C_6$ alkyl, optionally at least mono-substituted phenyl, —O-phenyl, and 5- to 6-membered heteroaryl.

If one or more of the rings of a mono- or polycyclic aromatic ring system contain one or more heteroatoms, these heteroatoms—like the heteroatoms of the previously mentioned 5- to 6-membered heteroaryl—can preferably be chosen from the group consisting of nitrogen, sulphur and oxygen.

If the previously mentioned phenyl radical is itself substituted by one or more substituents, each one of the substituents may be preferably chosen from the group consisting of fluorine, chlorine, bromine, linear or branched $C_1$-$C_6$ alkyl, linear or branched $C_1$-$C_6$ alkoxy, linear or branched $C_1$-$C_6$ alkylthio, trifluoromethyl radical, cyano radical and an $NR^{12}R^{13}$ radical, wherein $R^{12}$ and $R^{13}$, identical or different, are hydrogen or linear or branched $C_1$-$C_6$ alkyl.

If the previously mentioned alkylene, alkenylene or alkynylene group is substituted by one or more substituents, each of these substituents can preferably be chosen from the group consisting of hydroxy, halogen, linear or branched $C_1$-$C_6$ alkyl, linear or branched $C_1$-$C_6$ alkoxy, linear or branched $C_1$-$C_6$ perfluoroalkyl, linear or branched $C_1$-$C_6$ perfluoroalkoxy or an optionally at least mono-substituted phenyl radical. If said phenyl radical is itself substituted by one or more substituents, each one of these substituents can preferably be chosen from the group consisting of fluorine, chlorine, bromine, linear or branched $C_1$-$C_6$ alkyl, linear or branched $C_1$-$C_6$ alkoxy, linear or branched $C_1$-$C_6$ alkylthio, trifluoromethyl radical, cyano radical and a $NR^{12}R^{13}$ radical, wherein $R^{12}$ and $R^{13}$, identical or different, each represent hydrogen or linear or branched $C_1$-$C_6$ alkyl.

If one or more of the substituents $R^2$, $R^3$, $R^4$, $R^5$ and $R^6$ represents an alcoxy radical, said radical may have 1 to 6, preferably 1 to 3 carbon atoms.

Those skilled in the art understand that the term "condensed" indicates that the condensed rings share more than one atom. The terms "annulated" or "fused" may also be used for this type of bonding.

Sulfonamide derivatives of general formula (Ia) are preferred, wherein $R^1$ represents a —$NR^8R^9$ radical or a saturated or unsaturated, optionally at least mono-substituted 5- or 6-membered cycloaliphatic radical which may optionally contain at least one heteroatom as a ring member and/or which may be condensed with a saturated or unsaturated, optionally at least mono-substituted mono- or bicyclic cycloaliphatic ring system, which may optionally contain at least one heteroatom as a ring member, whereby the rings of the ring system are 5- or 6-membered, more preferably $R^1$ represents an —$NR^8R^9$ radical or a radical chosen from the group consisting of

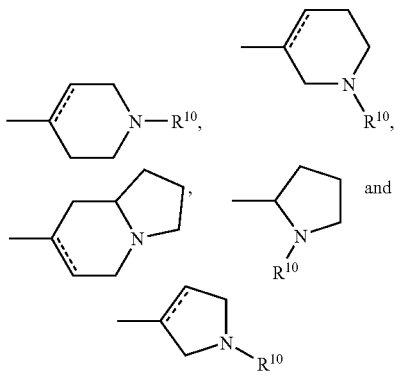

wherein, if present, the dotted line is an optional chemical bond, and $R^{10}$ is hydrogen, a linear or branched $C_1$-$C_6$ alkyl radical or a benzyl radical, preferably hydrogen or a $C_1$-$C_2$ alkyl radical and $R^2$-$R^9$, A and n are defined as above.

Sulfonamide derivatives of general formula (Ia) are also preferred, wherein $R^2$, $R^3$, $R^4$, $R^5$ and $R^6$, identical or different, each represent hydrogen, a linear or branched, optionally at least mono-substituted $C_1$-$C_6$ alkyl radical, a linear or branched, optionally at least mono-substituted $C_2$-$C_6$ alkenyl radical or a linear or branched, optionally at least mono-substituted $C_2$-$C_6$ alkynyl radical, more preferably $R^2$, $R^3$, $R^4$, $R^5$ and $R^6$, identical or different, each represent hydrogen or a linear or branched, optionally at least mono-substituted, $C_1$-$C_6$ alkyl radical, even more preferably $R^2$, $R^3$, $R^4$, $R^5$ and $R^6$ each represent hydrogen or a $C_1$-$C_2$ alkyl radical and $R^1$, $R^7$-$R^9$, A and n are defined as above.

Sulfonamide derivatives of general formula (Ia) are also preferred, wherein $R^7$ represents hydrogen, a linear or branched, optionally at least mono-substituted $C_1$-$C_6$ alkyl radical, a linear or branched, optionally at least mono-substituted $C_2$-$C_6$ alkenyl radical or a linear or branched, optionally at least mono-substituted $C_2$-$C_6$ alkynyl radical, more preferably $R^7$ represents hydrogen or a linear or branched, optionally at least mono-substituted $C_1$-$C_6$ alkyl radical, even more preferably $R^7$ represents hydrogen or a $C_1$-$C_2$ alkyl radical and $R^1$-$R^6$, $R^8$, $R^9$, A and n are defined as above.

Furthermore, sulfonamide derivatives of general formula (Ia) are also preferred, wherein $R^8$ and $R^9$, identical or different, each represent hydrogen, a linear or branched, optionally at least mono-substituted $C_1$-$C_{10}$ alkyl radical, a linear or branched, optionally at least mono-substituted $C_2$-$C_{10}$ alkenyl radical or a linear or branched, optionally at least mono-substituted $C_2$-$C_{10}$ alkynyl radical, with the proviso that $R^8$ and $R^9$ do not represent hydrogen at the same time, and if one of them, $R^8$ or $R^9$, represents a saturated or unsaturated, linear or branched, optionally at least mono-substituted $C_1$-$C_4$ aliphatic radical, the other one represents a saturated or unsaturated, linear or branched, optionally at least mono-substituted aliphatic radical with at least five carbon atoms, or $R^8$ and $R^9$, together with the bridging nitrogen atom form a saturated or unsaturated, optionally at least mono-substituted 5- or 6-membered heterocyclic ring, which may contain at least one additional heteroatom as a ring member and/or which may be condensed with a saturated or unsaturated, optionally at least mono-substituted mono- or bicyclic cycloaliphatic ring system, which may optionally contain at least one heteroatom as a ring member, whereby the rings of the ring system are 5- 6- or 7-membered and $R^1$-$R^7$, A and n are defined as above.

Particularly preferred is the use of sulfonamide derivatives of general formula (Ia), wherein $R^8$ and $R^9$, identical or different, each represent hydrogen or a linear or branched $C_1$-$C_{10}$ alkyl radical, with the proviso that $R^8$ and $R^9$ do not represent hydrogen at the same time, and if one of them, $R^8$ or $R^9$, represents a saturated or unsaturated, linear or branched, optionally at least mono-substituted $C_1$-$C_4$ aliphatic radical, the other one represents a saturated or unsaturated, linear or branched, optionally at least mono-substituted aliphatic radical with at least five carbon atoms, or $R^8$ and $R^9$ together with the bridging nitrogen atom form a radical chosen from the group consisting of

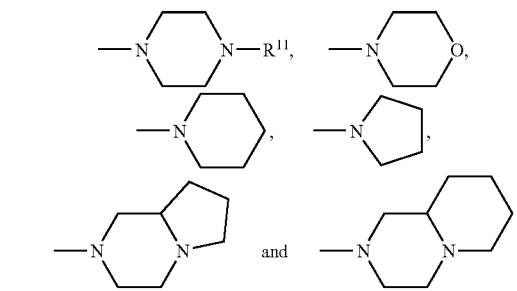

wherein $R^{11}$, if present, represents hydrogen, a linear or branched $C_1$-$C_6$ alkyl radical or a benzyl radical, preferably hydrogen, or a $C_1$-$C_2$ alkyl radical, and $R^1$-$R^7$, A and n are defined as above.

Furthermore, sulfonamide derivatives of general formula (Ia) are preferred, wherein A represents an optionally at least mono-substituted mono- or polycyclic aromatic ring system, wherein the ring(s) is/are 5- or 6-membered, which may be bonded via an optionally at least mono-substituted $C_1$-$C_6$ alkylene group, an optionally at least mono-substituted $C_2$-$C_6$ alkenylene group or an optionally at least mono-substituted $C_2$-$C_6$ alkynylene group and/or wherein the ring(s) may contain at least one heteroatom as a ring member, preferably A represents an optionally at least mono-substituted mono- or polycyclic aromatic ring system, wherein the ring(s) is/are 5- or 6-membered and wherein one or more of the rings contain at least one heteroatom, or a radical chosen from the group consisting of

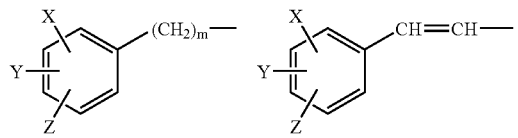

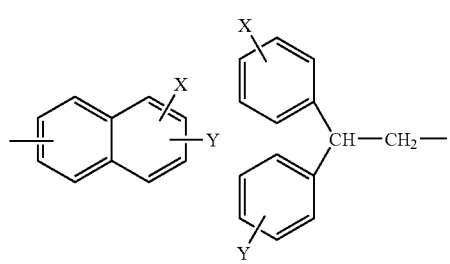

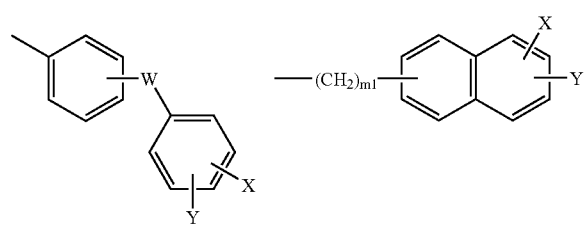

wherein X, Y, Z, independently from one another, each represent a radical selected from the group consisting of hydrogen, fluorine, chlorine, bromine, linear or branched $C_1$-$C_6$ alkyl, linear or branched $C_1$-$C_6$ alkoxy, linear or branched $C_1$-$C_6$ alkylthio, a trifluoromethyl radical, a cyano radical and a —$NR^{12}R^{13}$ radical, wherein $R^{12}$ and $R^{13}$, identical or different, each represent hydrogen or linear or branched $C_1$-$C_6$ alkyl, W represents a single chemical bond between the two rings, a $CH_2$, O, S group or a $NR^{14}$ radical, wherein $R^{14}$ is hydrogen or a linear or branched $C_1$-$C_6$ alkyl, m is 0, 1, 2, 3 or 4 and m1 is 1 or 2, preferably 2, and $R^1$-$R^9$ and n are defined as above.

Furthermore, sulfonamide derivatives of general formula (Ia) are preferred, wherein A represents an optionally at least mono-substituted mono- or polycyclic aromatic ring system, wherein the ring(s) is/are 5- or 6-membered, which may be bonded via an optionally at least mono-substituted $C_1$-$C_6$ alkylene group, an optionally at least mono-substituted $C_2$-$C_6$ alkenylene group or an optionally at least mono-substituted $C_2$-$C_6$ alkynylene group, and/or wherein the ring(s) may contain at least one heteroatom as a ring member, more preferably A represents an optionally at least mono-substituted mono- or polycyclic aromatic ring system, wherein the ring(s) is/are 5- or 6-membered and wherein one or more of the rings contain at least one heteroatom, or a radical chosen from the group consisting of

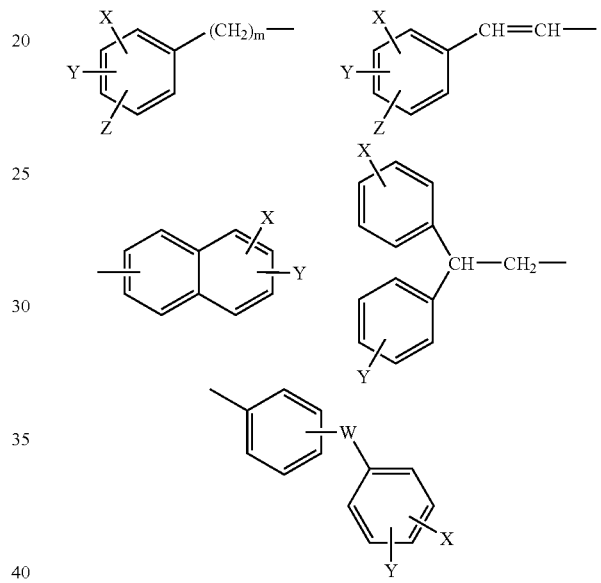

wherein X, Y, Z, independently from one another, each represent a radical selected from the group consisting of hydrogen, fluorine, chlorine, bromine, linear or branched $C_1$-$C_6$ alkyl, linear or branched $C_1$-$C_6$ alkoxy, linear or branched $C_1$-$C_6$ alkylthio, a trifluoromethyl radical, a cyano radical and a —$NR^{12}R^{13}$ radical, wherein $R^{12}$ and $R^{13}$, identical or different, each represent hydrogen or linear or branched $C_1$-$C_6$ alkyl, W represents a single chemical bond between the two rings, a $CH_2$, O, S group or a $NR^{14}$ radical, wherein $R^{14}$ is hydrogen or a linear or branched $C_1$-$C_6$ alkyl, and m is 0, 1, 2, 3 or 4.

and $R^1$-$R^9$ and n are defined as above.

Furthermore, sulfonamide derivatives of general formula (Ia) are preferred, wherein A a heteroaryl radical selected from the group consisting of benzo[b]thiophenyl and imidazo[2,1-b]thiazolyl which may be substituted by 1, 2 or 3 substituents selected from the group consisting of chlorine, methyl and phenyl and/or which may be bonded via a $C_{1-2}$ alkylene group, or a radical chosen from the group consisting of

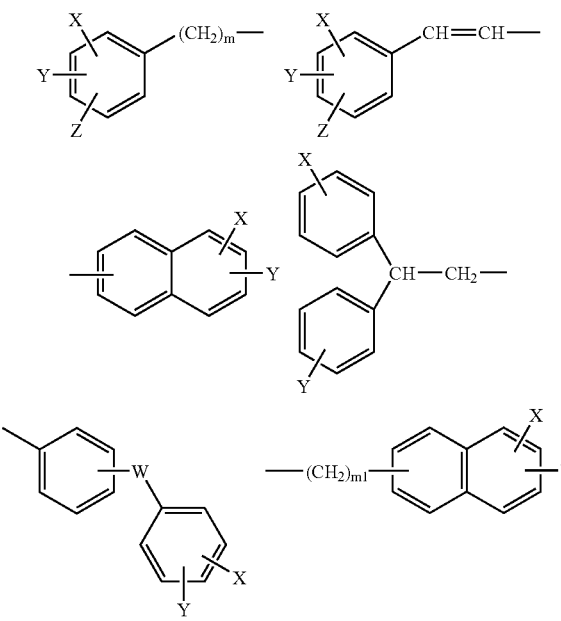

wherein X, Y, Z, independently from one another, each represent a radical selected from the group consisting of hydrogen, fluorine, chlorine, bromine, linear or branched $C_1$-$C_6$ alkyl, linear or branched $C_1$-$C_6$ alkoxy, linear or branched $C_1$-$C_6$ alkylthio, a trifluoromethyl radical, a cyano radical and a —$NR^{12}R^{13}$ radical, wherein $R^{12}$ and $R^{13}$, identical or different, each represent hydrogen or linear or branched $C_1$-$C_6$ alkyl, W represents a single chemical bond between the two rings, a $CH_2$, O, S group or a $NR^{14}$ radical, wherein $R^{14}$ is hydrogen or a linear or branched $C_1$-$C_6$ alkyl, m is 0, 1, 2, 3 or 4 and m1 is 1 or 2, preferably 2, and $R^1$-$R^9$ and n are defined as above.

Furthermore sulfonamide derivatives of general formula (Ia) are preferred, wherein n is 0, 1, 2, 3 or 4; preferably n is 1 or 2; more preferably n is 2 and $R^1$ to $R^9$ and A are defined as above.

The most preferred compounds general formula (Ia) are selected from the group consisting of

[5] 5-chloro-3-methyl-N-(1-(2-(pyrrolidin-1-yl)ethyl)-1H-indol-7-yl)-benzo[b]thiophen-2-sulfonamide,

[6] N-(1-(2-(pyrrolidin-1-yl)ethyl)-1H-indol-7-yl)naphthalene-1-sulfonamide,

[7] 6-chloro-N-(1-(2-(pyrrolidin-1-yl)ethyl)-1H-indol-7-yl) imidazo[2,1-b]thiazole-5-sulfonamide and

[8] 2-(naphth-1-yl)-N-(1-(2-(pyrrolidin-1-yl)ethyl)-1H-indol-7-yl)ethansulfonamide and their corresponding salts and solvates.

Furthermore, sulfonamide derivatives of general formula (Ib) are also preferred $R^2$, $R^3$, $R^4$, $R^5$ and $R^6$, identical or different, each represent hydrogen, a linear or branched, optionally at least mono-substituted $C_1$-$C_6$ alkyl radical, a linear or branched $C_1$-$C_6$ alkoxy radical, a linear or branched, optionally at least mono-substituted $C_2$-$C_6$ alkenyl radical or a linear or branched, optionally at least mono-substituted $C_2$-$C_6$ alkynyl radical, more preferably $R^2$, $R^3$, $R^4$, $R^5$ and $R^6$, identical or different, each represent hydrogen or a linear or branched, optionally at least mono-substituted, $C_1$-$C_6$ alkyl radical, even more preferably $R^2$, $R^3$, $R^4$, $R^5$ and $R^6$ each represent hydrogen or a $C_1$-$C_2$ alkyl radical and $R^1$, $R^7$-$R^9$, A and n are defined as above.

Sulfonamide derivatives of general formula (Ib) are also preferred, wherein $R^7$ represents hydrogen, a linear or branched, optionally at least mono-substituted $C_1$-$C_6$ alkyl radical, a linear or branched, optionally at least mono-substituted $C_2$-$C_6$ alkenyl radical or a linear or branched, optionally at least mono-substituted $C_2$-$C_6$ alkynyl radical, more preferably $R^7$ represents hydrogen or a linear or branched, optionally at least mono-substituted $C_1$-$C_6$ alkyl radical, even more preferably $R^7$ represents hydrogen or a $C_1$-$C_2$ alkyl radical and $R^1$-$R^6$, $R^8$, $R^9$, A and n are defined as above.

Furthermore, sulfonamide derivatives of general formula (Ib) are also preferred, wherein $R^8$ and $R^9$, identical or different, each represent hydrogen or a linear or branched, optionally at least mono-substituted $C_1$-$C_4$ alkyl radical and $R^1$-$R^7$, A and n are defined as above.

Particularly preferred are sulfonamide derivatives of general formula (Ib) wherein $R^8$ and $R^9$, identical or different, each represent hydrogen or a $C_1$-$C_2$ alkyl radical, with the proviso that $R^8$ and $R^9$ are not hydrogen at the same time, and $R^1$-$R^7$, A and n are defined as above.

Furthermore, sulfonamide derivatives of general formula (Ib) are preferred, wherein A represents an optionally at least mono-substituted mono- or polycyclic aromatic ring system, wherein the ring(s) is/are 5- or 6-membered, which may be bonded via an optionally at least mono-substituted $C_1$-$C_6$ alkylene group, an optionally at least mono-substituted $C_2$-$C_6$ alkenylene group or an optionally at least mono-substituted $C_2$-$C_6$ alkynylene group and/or wherein the ring(s) may contain at least one heteroatom as a ring member, preferably A represents an optionally at least mono-substituted mono- or polycyclic aromatic ring system, wherein the ring(s) is/are 5- or 6-membered and wherein one or more of the rings contain at least one heteroatom, or a radical chosen from the group consisting of

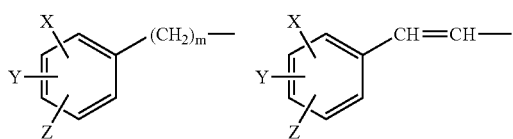

-continued

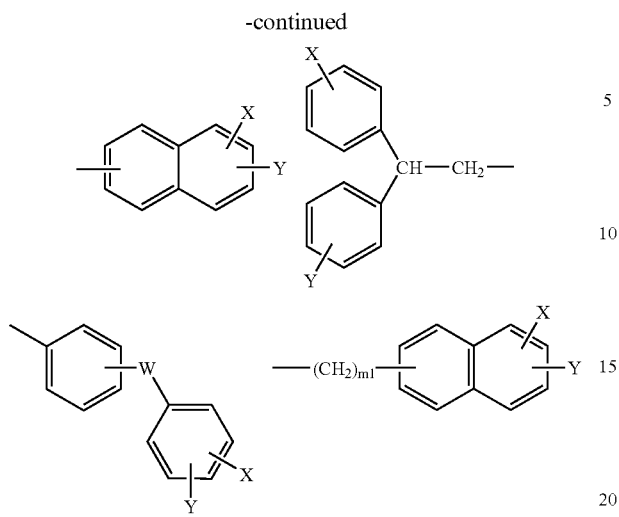

wherein X, Y, Z, independently from one another, each represent a radical selected from the group consisting of hydrogen, fluorine, chlorine, bromine, linear or branched $C_1$-$C_6$ alkyl, linear or branched $C_1$-$C_6$ alkoxy, linear or branched $C_1$-$C_6$ alkylthio, a trifluoromethyl radical, a cyano radical and a —$NR^{12}R^{13}$ radical, wherein $R^{12}$ and $R^{13}$, identical or different, each represent hydrogen or linear or branched $C_1$-$C_6$ alkyl, W represents a single chemical bond between the two rings, a $CH_2$, O, S group or a $NR^{14}$ radical, wherein $R^{14}$ is hydrogen or a linear or branched $C_1$-$C_6$ alkyl, m is 0, 1, 2, 3 or 4 and m1 is 1 or 2, preferably 2, and $R^1$-$R^9$ and n are defined as above.

Furthermore, sulfonamide derivatives of general formula (Ib) are preferred, wherein A represents an optionally at least mono-substituted mono- or polycyclic aromatic ring system, wherein the ring(s) is/are 5- or 6-membered, which may be bonded via an optionally at least mono-substituted $C_1$-$C_6$ alkylene group, an optionally at least mono-substituted $C_2$-$C_6$ alkenylene group or an optionally at least mono-substituted $C_2$-$C_6$ alkynylene group, and/or wherein the ring(s) may contain at least one heteroatom as a ring member, more preferably A represents an optionally at least mono-substituted mono- or polycyclic aromatic ring system, wherein the ring(s) is/are 5- or 6-membered and wherein one or more of the rings contain at least one heteroatom, or a radical chosen from the group consisting of

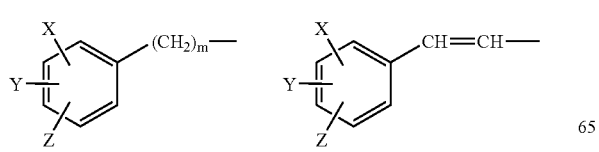

-continued

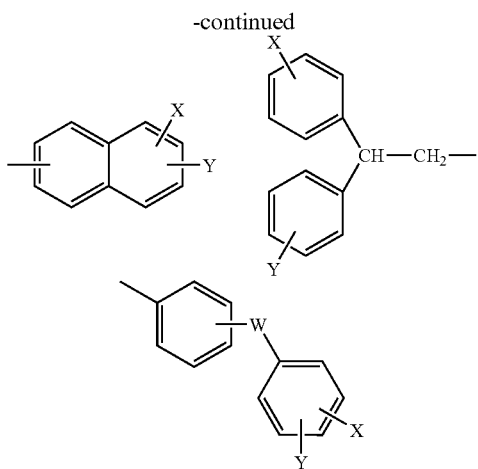

wherein X, Y, Z, independently from one another, each represent a radical selected from the group consisting of hydrogen, fluorine, chlorine, bromine, linear or branched $C_1$-$C_6$ alkyl, linear or branched $C_1$-$C_6$ alkoxy, linear or branched $C_1$-$C_6$ alkylthio, a trifluoromethyl radical, a cyano radical and a —$NR^{12}R^{13}$ radical, wherein $R^{12}$ and $R^{13}$, identical or different, each represent hydrogen or linear or branched $C_1$-$C_6$ alkyl, W represents a single chemical bond between the two rings, a $CH_2$, O, S group or a $NR^{14}$ radical, wherein $R^{14}$ is hydrogen or a linear or branched $C_1$-$C_6$ alkyl, and m is 0, 1, 2, 3 or 4.

and $R^1$-$R^9$ and n are defined as above.

Furthermore, sulfonamide derivatives of general formula (Ib) are preferred, wherein A a heteroaryl radical selected from the group consisting of benzo[b]thiophenyl and imidazo[2,1-b]thiazolyl which may be substituted by 1, 2 or 3 substituents selected from the group consisting of chlorine, methyl and phenyl and/or which may be bonded via a $C_{1-2}$ alkylene group, or a radical chosen from the group consisting of

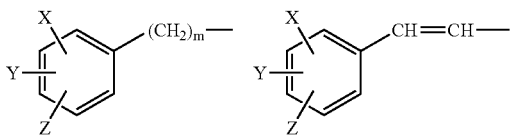

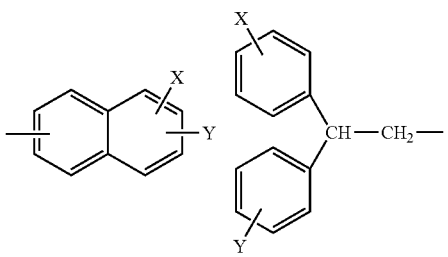

-continued

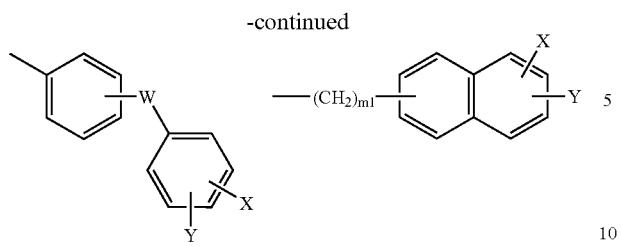

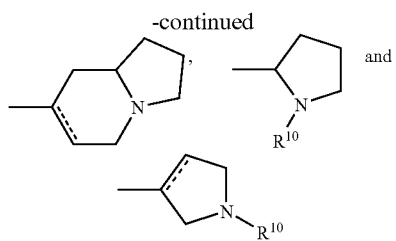
and

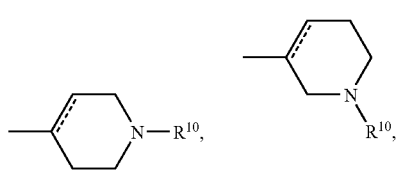

wherein X, Y, Z, independently from one another, each represent a radical selected from the group consisting of hydrogen, fluorine, chlorine, bromine, linear or branched $C_1$-$C_6$ alkyl, linear or branched $C_1$-$C_6$ alkoxy, linear or branched $C_1$-$C_6$ alkylthio, a trifluoromethyl radical, a cyano radical and a —$NR^{12}R^{13}$ radical, wherein $R^{12}$ and $R^{13}$, identical or different, each represent hydrogen or linear or branched $C_1$-$C_6$ alkyl, W represents a single chemical bond between the two rings, a $CH_2$, O, S group or a $NR^{14}$ radical, wherein $R^{14}$ is hydrogen or a linear or branched $C_1$-$C_6$ alkyl, m is 0, 1, 2, 3 or 4 and m1 is 1 or 2, preferably 2, and $R^1$-$R^9$ and n are defined as above.

Furthermore sulfonamide derivatives of general formula (Ib) are preferred, wherein n is 0, 1, 2, 3 or 4; preferably n is 1 or 2; more preferably n is 2 and $R^1$ to $R^9$ and A are defined as above.

Those most preferred compounds of general formula (Ib) are selected from the group consisting of

[1] N-[1-(2-dimethylaminoethyl)-1H-indole-7-yl]-naphtalene-1-sulfonamide,

[2] N-[1-(2-dimethylaminoethyl)-1H-indole-7-yl]-5-chloro-3-methylbenzo[b]thiophene-2-sulfonamide,

[3] N-[1-(2-dimethylaminoethyl)-1H-indole-7-yl]-4-phenyl-benzenesulfonamide and

[4] N-[1-(2-dimethylaminoethyl)-1H-indole-7-yl]-6-chloro-imidazo[2,1-b]thiazole-5-sulfonamide and their corresponding salts and solvates.

Sulfonamide derivatives of general formula (Ic) are preferred, wherein $R^1$ represents a —$NR^8R^9$ radical or a saturated or unsaturated, optionally at least mono-substituted 5- or 6-membered cycloaliphatic radical which may optionally contain at least one heteroatom as a ring member and/or which may be condensed with a saturated or unsaturated, optionally at least mono-substituted mono- or bicyclic cycloaliphatic ring system, which may optionally contain at least one heteroatom as a ring member, whereby the rings of the ring system are 5- or 6-membered, more preferably $R^1$ represents an —$NR^8R^9$ radical or a radical chosen from the group consisting of wherein, if present, the dotted line is an optional chemical bond, and $R^{10}$ is hydrogen, a linear or branched $C_1$-$C_6$ alkyl radical or a benzyl radical, preferably hydrogen or a $C_1$-$C_2$ alkyl radical and $R^2$-$R^9$, A and n are defined as above.

Sulfonamide derivatives of general formula (Ic) are also preferred, wherein $R^2$, $R^3$, $R^4$, $R^1$ and $R^6$, identical or different, each represent hydrogen, a linear or branched, optionally at least mono-substituted $C_1$-$C_6$ alkyl radical, a linear or branched, optionally at least mono-substituted $C_2$-$C_6$ alkenyl radical or a linear or branched, optionally at least mono-substituted $C_2$-$C_6$ alkynyl radical, more preferably $R^2$, $R^3$, $R^4$, $R^5$ and $R^6$, identical or different, each represent hydrogen or a linear or branched, optionally at least mono-substituted, $C_1$-$C_6$ alkyl radical, even more preferably $R^2$, $R^3$, $R^4$, $R^5$ and $R^6$ each represent hydrogen and $R^1$, $R^7$-$R^9$, A and n are defined as above.

Sulfonamide derivatives of general formula (Ic) are also preferred, wherein $R^7$ represents hydrogen, a linear or branched, optionally at least mono-substituted $C_1$-$C_6$ alkyl radical, a linear or branched, optionally at least mono-substituted $C_2$-$C_6$ alkenyl radical or a linear or branched, optionally at least mono-substituted $C_2$-$C_6$ alkynyl radical, more preferably $R^7$ represents hydrogen or a linear or branched, optionally at least mono-substituted $C_1$-$C_6$ alkyl radical, even more preferably $R^7$ represents hydrogen or a $C_1$-$C_2$ alkyl radical and $R^1$-$R^6$, $R^8$, $R^9$, A and n are defined as above.

Furthermore, sulfonamide derivatives of general formula (Ic) are also preferred, wherein $R^8$ and $R^9$, identical or different, each represent hydrogen, a linear or branched, optionally at least mono-substituted $C_1$-$C_{10}$ alkyl radical, a linear or branched, optionally at least mono-substituted $C_2$-$C_{10}$ alkenyl radical or a linear or branched, optionally at least mono-substituted $C_2$-$C_{10}$ alkynyl radical, or $R^8$ and $R^9$, together with the bridging nitrogen atom form a saturated or unsaturated, optionally at least mono-substituted 5- or 6-membered heterocyclic ring, which may contain at least one additional heteroatom as a ring member and/or which may be condensed with a saturated or unsaturated, optionally at least mono-substituted mono- or bicyclic cycloaliphatic ring system, which may optionally contain at least one heteroatom as a ring member, whereby the rings of the ring system are 5- 6- or 7-membered and $R^1$-$R^7$, A and n are defined as above.

Particularly preferred is the use of sulfonamide derivatives of general formula (Ic), wherein $R^8$ and $R^9$, identical or different, each represent hydrogen or a linear or branched $C_1$-$C_{10}$ alkyl radical, or $R^8$ and $R^9$ together with the bridging nitrogen atom form a radical chosen from the group consisting of

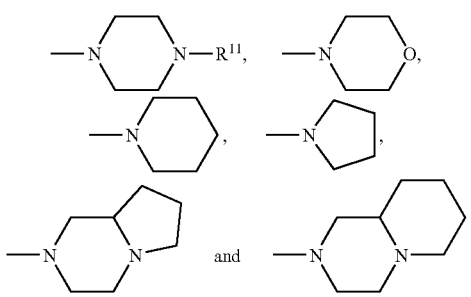

wherein $R^{11}$, if present, represents hydrogen, a linear or branched $C_1$-$C_6$ alkyl radical or a benzyl radical, preferably hydrogen, or a $C_1$-$C_2$ alkyl radical, and $R^1$-$R^7$, A and n are defined as above.

Furthermore, sulfonamide derivatives of general formula (Ic) are preferred, wherein A represents an optionally at least mono-substituted mono- or polycyclic aromatic ring system, wherein the ring(s) is/are 5- or 6-membered, which may be bonded via an optionally at least mono-substituted $C_1$-$C_6$ alkylene group, an optionally at least mono-substituted $C_2$-$C_6$ alkenylene group or an optionally at least mono-substituted $C_2$-$C_6$ alkynylene group and/or wherein the ring(s) may contain at least one heteroatom as a ring member, preferably A represents an optionally at least mono-substituted mono- or polycyclic aromatic ring system, wherein the ring(s) is/are 5- or 6-membered and wherein one or more of the rings contain at least one heteroatom, or a radical chosen from the group consisting of

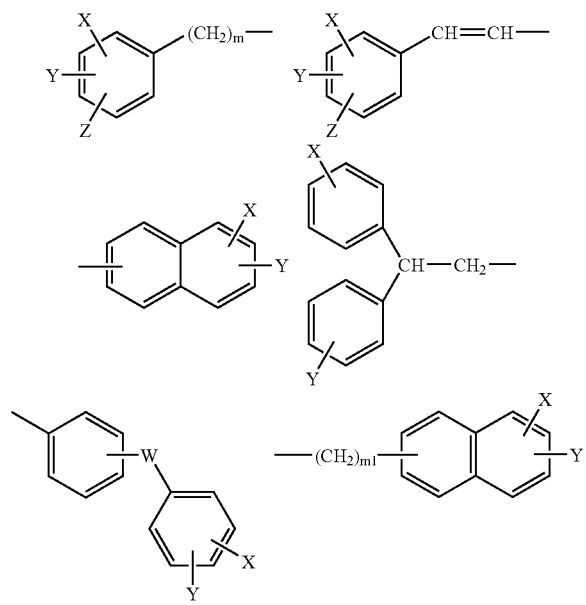

wherein X, Y, Z, independently from one another, each represent a radical selected from the group consisting of hydrogen, fluorine, chlorine, bromine, linear or branched $C_1$-$C_6$ alkyl, linear or branched $C_1$-$C_6$ alkoxy, linear or branched $C_1$-$C_6$ alkylthio, a trifluoromethyl radical, a cyano radical and a —$NR^{12}R^{13}$ radical, wherein $R^{12}$ and $R^{13}$, identical or different, each represent hydrogen or linear or branched $C_1$-$C_6$ alkyl, W represents a single chemical bond between the two rings, a $CH_2$, O, S group or a $NR^{14}$ radical, wherein $R^{14}$ is hydrogen or a linear or branched $C_1$-$C_6$ alkyl, m is 0, 1, 2, 3 or 4 and m1 is 1 or 2, preferably 2, and $R^1$-$R^9$ and n are defined as above.

Furthermore, sulfonamide derivatives of general formula (Ic) are preferred, wherein A represents an optionally at least mono-substituted mono- or polycyclic aromatic ring system, wherein the ring(s) is/are 5- or 6-membered, which may be bonded via an optionally at least mono-substituted $C_1$-$C_6$ alkylene group, an optionally at least mono-substituted $C_2$-$C_6$ alkenylene group or an optionally at least mono-substituted $C_2$-$C_6$ alkynylene group, and/or wherein the ring(s) may contain at least one heteroatom as a ring member, more preferably A represents an optionally at least mono-substituted mono- or polycyclic aromatic ring system, wherein the ring(s) is/are 5- or 6-membered and wherein one or more of the rings contain at least one heteroatom, or a radical chosen from the group consisting of

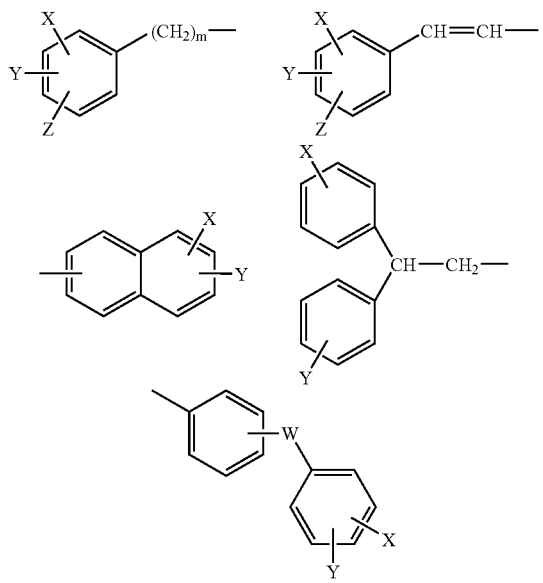

wherein X, Y, Z, independently from one another, each represent a radical selected from the group consisting of hydrogen, fluorine, chlorine, bromine, linear or branched $C_1$-$C_6$ alkyl, linear or branched $C_1$-$C_6$ alkoxy, linear or branched $C_1$-$C_6$ alkylthio, a trifluoromethyl radical, a cyano radical and a —$NR^{12}R^{13}$ radical, wherein $R^{12}$ and $R^{13}$, identical or different, each represent hydrogen or linear or branched $C_1$-$C_6$ alkyl, W represents a single chemical bond between the two rings, a $CH_2$, O, S group or a $NR^{14}$ radical, wherein $R^{14}$ is hydrogen or a linear or branched $C_1$-$C_6$ alkyl, and m is 0, 1, 2, 3 or 4.

and $R^1$-$R^9$ and n are defined as above.

Furthermore, sulfonamide derivatives of general formula (Ic) are preferred, wherein A a heteroaryl radical selected from the group consisting of benzo[b]thiophenyl and imidazo[2,1-b]thiazolyl which may be substituted by 1, 2 or 3 substituents selected from the group consisting of chlorine, methyl and phenyl and/or which may be bonded via a $C_{1-2}$ alkylene group, or a radical chosen from the group consisting of

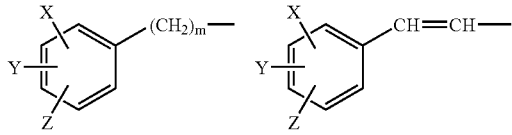

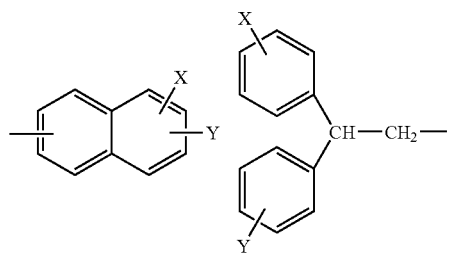

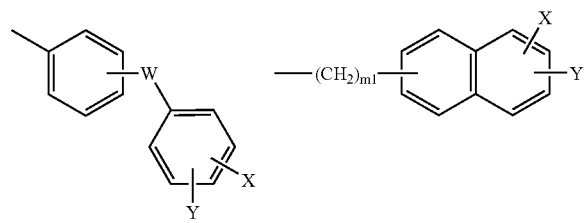

wherein X, Y, Z, independently from one another, each represent a radical selected from the group consisting of hydrogen, fluorine, chlorine, bromine, linear or branched $C_1$-$C_6$ alkyl, linear or branched $C_1$-$C_6$ alkoxy, linear or branched $C_1$-$C_6$ alkylthio, a trifluoromethyl radical, a cyano radical and a —$NR^{12}R^{13}$ radical, wherein $R^{12}$ and $R^{13}$, identical or different, each represent hydrogen or linear or branched $C_1$-$C_6$ alkyl, W represents a single chemical bond between the two rings, a $CH_2$, O, S group or a $NR^{14}$ radical, wherein $R^{14}$ is hydrogen or a linear or branched $C_1$-$C_6$ alkyl, m is 0, 1, 2, 3 or 4 and m1 is 1 or 2, preferably 2, and $R^1$-$R^9$ and n are defined as above.

Furthermore sulfonamide derivatives of general formula (Ic) are preferred, wherein n is 0, 1, 2, 3 or 4; preferably n is 1 or 2; more preferably n is 2 and $R^1$ to $R^9$ and A are defined as above.

Another aspect of the present invention are compounds of general formula (Ic),

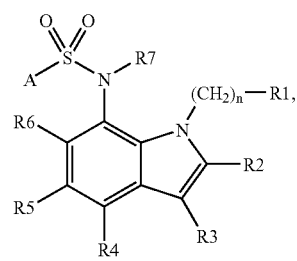

wherein $R^1$ is a —$NR^8R^9$ radical, $R^2$, $R^3$, $R^4$, $R^5$ and $R^6$ each represent hydrogen, $R^7$ represents hydrogen, $R^8$ and $R^9$, identical or different, each represent methyl, ethyl, n-propyl or iso-propyl, more preferably methyl, or $R^8$ and $R^9$ together with the bridging nitrogen atom form a 5- or 6-membered heterocyclic ring, more preferably form a pyrrolidine or piperidine ring, A represents an aryl or heteroaryl radical selected from the group consisting of phenyl, naphthyl, benzo[b]thiophenyl and imidazo[2,1-b]thiazolyl which may be substituted by 1, 2 or 3 substituents selected from the group consisting of chlorine, methyl and phenyl and/or which may be bonded via a $C_{1-2}$ alkylene group, and n is 2;

optionally in form of one of its stereoisomers, preferably enantiomers or diastereomers, its racemate or in form of a mixture of at least two of its stereoisomers, preferably enantiomers or diastereomers, in any mixing ratio, or a salt thereof, preferably a corresponding, physiologically acceptable salt thereof, or a corresponding solvate thereof.

The most preferred compounds general formula (Ic) are selected from the group consisting of

[1] N-[1-(2-dimethylaminoethyl)-1H-indole-7-yl]-naphtalene-1-sulfonamide,

[2] N-[1-(2-dimethylaminoethyl)-1H-indole-7-yl]-5-chloro-3-methylbenzo[b]thiophene-2-sulfonamide,

[3] N-[1-(2-dimethylaminoethyl)-1H-indole-7-yl]-4-phenyl-benzenesulfonamide and

[4] N-[1-(2-dimethylaminoethyl)-1H-indole-7-yl]-6-chloroimidazo[2,1-b]thiazole-5-sulfonamide

[5] 5-chloro-3-methyl-N-(1-(2-(pyrrolidin-1-yl)ethyl)-1H-indol-7-yl)-benzo[b]thiophen-2-sulfonamide,

[6] N-(1-(2-(pyrrolidin-1-yl)ethyl)-1H-indol-7-yl)naphthalene-1-sulfonamide,

[7] 6-chloro-N-(1-(2-(pyrrolidin-1-yl)ethyl)-1H-indol-7-yl) imidazo[2,1-b]thiazole-5-sulfonamide and

[8] 2-(naphth-1-yl)-N-(1-(2-(pyrrolidin-1-yl)ethyl)-1H-indol-7-yl)ethansulfonamide and their corresponding salts and solvates.

The present invention likewise refers to the salts, preferably the physiologically acceptable salts of the compounds of general formula (Ia) and/or (Ib) and/or of general formula (Ic), preferably the addition salts of mineral acids, more preferably of hydrochloric acid, hydrobromic acid acid, phosphoric acid, sulphuric acid, nitric acid, and the salts of organic acids, more preferably of citric acid, maleic acid acid, fumaric acid, tartaric acid or their derivatives, p-toluenesulphonic acid, methanesulphonic acid, camphorsulphonic acid, etc.

Below, the expression sulfonamide derivatives of general formula (I), to one or more compounds of general formula (Ia) and/or to one or more compounds of general formula (Ib) and/or to one or more compounds of general formula (Ic), respectively, and optionally in form of one of their stereoisomers, preferably enantiomers or diastereomers, their racemate, or in form of a mixture of at least two of their stereoisomers, preferably enantiomers or diastereomers, in any mixing ratio, or a salt thereof, preferably a corresponding physiologically acceptable salt thereof, or a corresponding solvate thereof.

Another aspect of the present invention consists of a process for preparing the new derivatives of general formula (I), wherein $R^1$-$R^9$, n and A have the previously indicated meaning, according to which at least one compound of general formula (II),

(II)

wherein A has the previously mentioned meaning, and X is an acceptable leaving group, preferably an halogen atom, more preferably chlorine; reacts with at least one substituted 7-aminoindole of general formula (III)

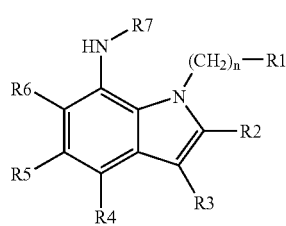

(III)

wherein $R^1$-$R^7$ and n have the previously indicated meaning, or one of their suitable protected derivatives, and, if necessary, the protective groups are removed, in order to obtain the corresponding sulfonamide derivative of general formula (I), which may be purified and/or isolated via conventional methods known in the prior art.

The reaction between the compounds of general formula (II) and (III) is usually carried out in the presence of an organic reaction medium, preferably in the presence of dialkyl ether, more preferably diethyl ether or a cyclic ether, more preferably tetrahydrofuran or dioxane, an halogenated organic hydrocarbon, more preferably methylene chloride or chloroform, an alcohol, more preferably methanol or ethanol, a dipolar aprotic solvent, more preferably acetonitrile, pyridine or dimethylformamide, or any other suitable reaction medium. Naturally, mixtures of at least two of the classes of the mentioned compounds or at least two compounds of one class may also be used.

The reaction is preferably carried out in the presence of a suitable base, for example, an inorganic base, more preferably alkaline metal hydroxides and alkaline metal carbonates, or in the presence of an organic base, more preferably triethylamine, N-ethyldiisopropylamine or pyridine.

The most suitable reaction temperatures range from 0° C. to room temperature, that is, approximately 25° C., and the reaction time is preferably from 5 minutes to 24 hours.

The resulting sulfonamide derivative of general formula (I) may be purified and/or isolated according to conventional methods known in the prior art.

Preferably, the sulfonamide derivatives of general formula (I) may be isolated by evaporating the reaction medium, adding water and, if necessary, adjusting the pH so that a solid which may be isolated by filtration is obtained; or the sulfonamide derivatives may be extracted with a water immiscible solvent, preferably chloroform, and be purified by chromatography or recrystallization in a suitable solvent.

The compounds of general formula (II) are commercially available, or they may be prepared according to standard methods known in the prior art, for example by methods similar to those described in the literature [E. E. Gilbert, Synthesis, 1969, 1, 3]. The compounds of general formula (III) may also be prepared according to standard methods known in the prior art, for example by methods similar to those described in: [Abou-Gharbia, Magid; Patel, Usha; Tokolics, Joseph; Freed, Meier. European Journal of Medicinal Chemistry (1988), 23(4), 373-7]. The respective literature descriptions are incorporated by reference and form part of the disclosure.

Another aspect of the present invention consists in a process for preparing the new sulfonamide derivatives of general formula (I), wherein $R^1$-$R^6$, $R^8$, $R^9$, n and A have the previously indicated meaning and $R^7$ is an alkyl radical, preferably a linear or branched, optionally at least mono-substituted $C_1$-$C_6$ alkyl radical by alkylation of a sulfonamide derivative of general formula (I), wherein $R^1$-$R^6$, $R^8$, $R^9$, n and A have the previously indicated meaning, and $R^7$ is a hydrogen atom, with an alkyl halogenide or dialkyl sulfate.

The alkylation reaction is carried out preferably in the presence of a suitable base, more preferably in the presence of alkaline metal hydroxides and alkaline metal carbonates, metal hydrides, metal alkoxides, even more preferably sodium methoxide or potassium tert-butoxide, organometallic compounds, even more preferably butyllithium or tert-butyllithium, in the presence of an organic reaction medium, more preferably dialkyl ether, even more preferably diethyl ether, or a cyclic ether, even more preferably tetrahydrofuran or dioxane, an hydrocarbon, even more preferably toluene, an alcohol, even more preferably methanol or ethanol, a dipolar aprotic solvent, even more preferably acetonitrile, pyridine or dimethylformamide, or any other suitable reaction medium. Naturally, mixtures of at least two of the classes of the mentioned compounds or at least two compounds of one class may also be used.

The most suitable reaction temperatures range from 0° C. to the boiling temperature of the reaction medium, and the reaction times are preferably from 1 to 24 hours.

Preferably, the resulting sulfonamide derivative of general formula (I) may be isolated by filtration, concentrating the filtrate under reduced pressure, adding water and, if necessary, adjusting the pH so that a solid which may be isolated by filtration is obtained; or the sulfonamide derivatives may be extracted with a water immiscible solvent, preferably chloroform, and be purified by chromatography or recrystallization in a suitable solvent.

The salts, preferably pharmaceutically acceptable salts of the compounds of general formula (I), may be prepared by means of conventional methods known in the prior art, preferably by reaction with a mineral acid, more preferably by reaction with hydrochloric acid, hydrobromic acid, phosphoric acid acid, sulphuric acid or nitric acid, or by reaction with organic acids, more preferably by reaction with citric acid, maleic acid, fumaric acid acid, tartaric acid, or their derivatives, p-toluenesulphonic acid, methanesulphonic acid, camphorsulphonic acid, etc., in a suitable solvent, preferably methanol, ethanol, diethyl ether, ethyl acetate, acetonitrile or acetone, and obtaining the resulting salts by using the usual techniques for the precipitation or crystallization of the corresponding salts.

The preferred physiologically acceptable salts of the sulfonamide derivatives of general formula (I) are the addition salts of mineral acids, more preferably of hydrochloric acid, hydrobromic acid, phosphoric acid, sulphuric acid acid or nitric acid, and the addition salts of organic acids, more preferably citric acid, maleic acid, fumaric acid, tartaric acid, or their derivatives, p-toluenesulphonic acid, methanesulphonic acid, camphorsulphonic acid, etc.

The solvates, preferably the physiologically acceptable solvates, more preferably hydrates, of the sulfonamide derivatives of general formula (I) or of the corresponding physiologically acceptable salts, may be prepared by methods known in the prior art.

During some of the synthetic sequences described in the preparation of the suitable reagents used, it may be necessary and/or desirable to protect sensitive or reactive groups in some of the molecules used. This may be carried out via the use of conventional protective groups preferably those described in the literature [Protective groups in Organic Chemistry, ed. J. F. W. McOmie, Plenum Press, 1973; T. W. Greene & P. G. M. Wuts, Protective Groups in Organic Chemistry, John Wiley & Sons, 1991]. The protective groups may be removed in the suitable subsequent stage by methods known in the prior art. The respective literature descriptions are incorporated by reference and form part of the disclosure.

If the sulfonamide derivatives of general formula (I) are obtained in form of a mixture of stereoisomers, preferably enantiomers or diastereomers, said mixtures may be separated via standard processes known in the prior art, for example chromatographic methods or crystallization with chiral agents.

Another aspect of the present invention is a medicament comprising at least one indol-7-yl sulfonamide derivative of general formula (I), optionally in form of one of its stereoisomers, preferably enantiomers or diastereomers, its racemate, or in form of a mixture of at least two of its stereoisomers, preferably enantiomers or diastereomers, in any mixing ratio, or a corresponding physiologically acceptable salt or a corresponding solvate, and optionally one or more pharmaceutically acceptable adjuvants.

This medicament is suitable for $5-HT_6$ receptor regulation, for the prophylaxis and/or treatment of a disorder or disease related to food intake, preferably for the regulation of appetite, for the maintenance, increase or reduction of body weight, for the prophylaxis and/or treatment of obesity, bulimia, anorexia, cachexia or type II diabetes (non insulin dependent diabetes mellitus), preferably type II diabetes caused by obesity, for the prophylaxis and/or treatment of gastrointestinal tract disorders, preferably irritable bowel syndrome, for cognitive enhancement, for the prophylaxis and/or treatment of disorders of the central nervous system, anxiety, panic disorders, depression, preferably bipolar disorders, cognitive memory disorders, senile dementia processes, neurodegenerative disorders, preferably Alzheimer's disease, Parkinson's disease, Huntington's disease and/or Multiple Sclerosis, schizophrenia, psychosis or infantile hyperkinesia (ADHD, attention deficit/hyperactivity disorder) and other disorders mediated by the $5-HT_6$ serotonin receptor in humans and/or in animals, preferably in mammals, more preferably in humans.

Another aspect of the present invention is a medicament comprising at least one indol-7-yl sulfonamide derivative of general formula (Ia), optionally in form of one of its stereoisomers, preferably enantiomers or diastereomers, its racemate, or in form of a mixture of at least two of its stereoisomers, preferably enantiomers or diastereomers, in any mixing ratio, or a corresponding physiologically acceptable salt or a corresponding solvate, and optionally one or more pharmaceutically acceptable adjuvants.

This medicament is suitable for $5-HT_6$ receptor regulation, for the prophylaxis and/or treatment of a disorder or disease related to food intake, preferably for the regulation of appetite, for the maintenance, increase or reduction of body weight, for the prophylaxis and/or treatment of obesity, bulimia, anorexia, cachexia or type II diabetes (non insulin dependent diabetes mellitus), preferably type II diabetes caused by obesity, for the prophylaxis and/or treatment of gastrointestinal tract disorders, preferably irritable bowel syndrome, for cognitive enhancement, for the prophylaxis and/or treatment of disorders of the central nervous system, anxiety, panic disorders, depression, preferably bipolar disorders, cognitive memory disorders, senile dementia processes, neurodegenerative disorders, preferably Alzheimer's disease, Parkinson's disease, Huntington's disease and/or Multiple Sclerosis, schizophrenia, psychosis or infantile hyperkinesia (ADHD, attention deficit/hyperactivity disorder), and other disorders mediated by the $5-HT_6$ serotonin receptor in humans and/or in animals, preferably in mammals, more preferably in humans, more suitable for $5-HT_6$ receptor regulation, for the prophylaxis and/or treatment of a disorder or disease related to food intake, preferably for the regulation of appetite, for the maintenance, increase or reduction of body weight, for the prophylaxis and/or treatment of obesity, bulimia, anorexia, cachexia or type II diabetes (non insulin dependent diabetes mellitus), preferably type II diabetes caused by obesity, for the prophylaxis and/or treatment of gastrointestinal tract disorders, preferably irritable bowel syndrome in humans and/or in animals, preferably in mammals, more preferably in humans.

Another aspect of the present invention is a medicament comprising at least one indol-7-yl sulfonamide derivative of general formula (Ib), optionally in form of one of its stereoisomers, preferably enantiomers or diastereomers, its racemate, or in form of a mixture of at least two of its stereoisomers, preferably enantiomers or diastereomers, in any mixing ratio, or a corresponding physiologically acceptable salt or a corresponding solvate, and optionally one or more pharmaceutically acceptable adjuvants.

This medicament is suitable for $5-HT_6$ receptor regulation, for the prophylaxis and/or treatment of a disorder or disease related to food intake, preferably for the regulation of appetite, for the maintenance, increase or reduction of body weight, for the prophylaxis and/or treatment of obesity, bulimia, anorexia, cachexia or type II diabetes (non insulin dependent diabetes mellitus), preferably type II diabetes caused by obesity, for the prophylaxis and/or treatment of gastrointestinal tract disorders, preferably irritable bowel syndrome, for cognitive enhancement, for the prophylaxis and/or treatment of disorders of the central nervous system, anxiety, panic disorders, depression, preferably bipolar disorders, cognitive memory disorders, senile dementia processes, neurodegenerative disorders, preferably Alzheimer's disease, Parkinson's disease, Huntington's disease and/or Multiple Sclerosis, schizophrenia, psychosis or infantile hyperkinesia (ADHD, attention deficit/hyperactivity disorder), and other disorders mediated by the 5-$HT_6$ serotonin receptor in humans and/or in animals, preferably in mammals, more preferably in humans, more suitable for cognitive enhancement, for the prophylaxis and/or treatment of disorders of the central nervous system, anxiety, panic disorders, depression, preferably bipolar disorders, cognitive memory disorders, senile dementia processes, neurodegenerative disorders, preferably Alzheimer's disease, Parkinson's disease, Huntington's disease and/or Multiple Sclerosis, schizophrenia, psychosis or infantile hyperkinesia (ADHD, attention deficit/hyperactivity disorder) in humans and/or in animals, preferably in mammals, more preferably in humans.

Another aspect of the present invention is a medicament comprising at least one indol-7-yl sulfonamide derivative of general formula (Ic), optionally in form of one of its stereoisomers, preferably enantiomers or diastereomers, its racemate, or in form of a mixture of at least two of its stereoisomers, preferably enantiomers or diastereomers, in any mixing ratio, or a corresponding physiologically acceptable salt or a corresponding solvate, and optionally one or more pharmaceutically acceptable adjuvants.

This medicament is suitable for 5-$HT_6$ receptor regulation, for the prophylaxis and/or treatment of a disorder or disease related to food intake, preferably for the regulation of appetite, for the maintenance, increase or reduction of body weight, for the prophylaxis and/or treatment of obesity, bulimia, anorexia, cachexia or type II diabetes (non insulin dependent diabetes mellitus), preferably type II diabetes caused by obesity, for the prophylaxis and/or treatment of gastrointestinal tract disorders, preferably irritable bowel syndrome, for cognitive enhancement, for the prophylaxis and/or treatment of disorders of the central nervous system, anxiety, panic disorders, depression, preferably bipolar disorders, cognitive memory disorders, senile dementia processes, neurodegenerative disorders, preferably Alzheimer's disease, Parkinson's disease, Huntington's disease and/or Multiple Sclerosis, schizophrenia, psychosis or infantile hyperkinesia (ADHD, attention deficit/hyperactivity disorder) and other disorders mediated by the 5-$HT_6$ serotonin receptor in humans and/or in animals, preferably in mammals, more preferably in humans.

The medicament obtained according to the present invention is particularly suitable for the administration to mammals, including man. The medicament may preferably be administered to all age groups, namely, children, adolescents and adults.

Another aspect of the present invention is the use of at least one sulfonamide derivative of general formula (I), optionally in form of one of its stereoisomers, preferably enantiomers or diastereomers, its racemate, or in form of a mixture of at least two of its stereoisomers, preferably enantiomers or diastereomers, in any mixing ratio, or a corresponding physiologically acceptable salt or a corresponding solvate, for the manufacture of a medicament for 5-$HT_6$ receptor regulation, for the prophylaxis and/or treatment of a disorder or disease related to food intake, preferably for the regulation of appetite, for the maintenance, increase or reduction of body weight, for the prophylaxis and/or treatment of obesity, bulimia, anorexia, cachexia or type II diabetes (non insulin dependent diabetes mellitus), preferably type II diabetes caused by obesity, for the prophylaxis and/or treatment of gastrointestinal tract disorders, preferably irritable bowel syndrome, for cognitive enhancement, for the prophylaxis and/or treatment of disorders of the central nervous system, anxiety, panic disorders, depression, preferably bipolar disorders, cognitive memory disorders, senile dementia processes, neurodegenerative disorders, preferably Alzheimer's disease, Parkinson's disease, Huntington's disease and/or Multiple Sclerosis, schizophrenia, psychosis or infantile hyperkinesia (ADHD, attention deficit/hyperactivity disorder) in humans and/or in animals, preferably in mammals, more preferably in humans.

Another aspect of the present invention is the use of at least one sulfonamide derivative of the previous general formula (Ia), optionally in form of one of its stereoisomers, preferably enantiomers or diastereomers, its racemate, or in form of a mixture of at least two of its stereoisomers, preferably enantiomers or diastereomers, in any mixing ratio, or a corresponding physiologically acceptable salt or a corresponding solvate, for the manufacture of a medicament for 5-$HT_6$ receptor regulation, for the prophylaxis and/or treatment of a disorder or disease related to food intake, preferably for the regulation of appetite, for the maintenance, increase or reduction of body weight, for the prophylaxis and/or treatment of obesity, bulimia, anorexia, cachexia or type II diabetes (non insulin dependent diabetes mellitus), preferably type II diabetes caused by obesity, for the prophylaxis and/or treatment of gastrointestinal tract disorders, preferably irritable bowel syndrome, for cognitive enhancement, for the prophylaxis and/or treatment of disorders of the central nervous system, anxiety, panic disorders, depression, preferably bipolar disorders, cognitive memory disorders, senile dementia processes, neurodegenerative disorders, preferably Alzheimer's disease, Parkinson's disease, Huntington's disease and/or Multiple Sclerosis, schizophrenia, psychosis or infantile hyperkinesia (ADHD, attention deficit/hyperactivity disorder) in humans and/or in animals, preferably in mammals, more preferably in humans, preferably for the manufacture of a medicament for 5-$HT_6$ receptor regulation, for the prophylaxis and/or treatment of a disorder or disease related to food intake, preferably for the regulation of appetite, for the maintenance, increase or reduction of body weight, for the prophylaxis and/or treatment of obesity, bulimia, anorexia, cachexia or type II diabetes (non insulin dependent diabetes mellitus), preferably type II diabetes caused by obesity, for the prophylaxis and/or treatment of gastrointestinal tract disorders, preferably irritable bowel syndrome.

Another aspect of the present invention is the use of at least one sulfonamide derivative of the previous general formula (Ib), optionally in form of one of its stereoisomers, preferably enantiomers or diastereomers, its racemate, or in form of a mixture of at least two of its stereoisomers, preferably enantiomers or diastereomers, in any mixing ratio, or a corresponding physiologically acceptable salt or a corresponding solvate, for the manufacture of a medicament for 5-$HT_6$ receptor regulation, for the prophylaxis and/or treatment of a disorder or disease related to food intake, preferably for the regulation of appetite, for the maintenance, increase or reduction of body weight, for the prophylaxis and/or treatment of obesity, bulimia, anorexia, cachexia or type II diabetes (non insulin dependent diabetes mellitus), preferably type II diabetes caused by obesity, for the prophylaxis and/or treatment of gastrointestinal tract disorders, preferably irritable bowel syndrome, for cognitive enhancement, for the prophylaxis and/or treatment of disorders of the central nervous system, anxiety, panic disorders, depression, preferably bipolar disorders, cognitive memory disorders, senile dementia processes, neurodegenerative disorders, preferably Alzheimer's disease, Parkinson's disease, Huntington's disease and/or Multiple Sclerosis, schizophrenia, psychosis or infantile hyperkinesia (ADHD, attention deficit/hyperactivity disorder), and other disorders mediated by the 5-HT$_6$ serotonin receptor in humans and/or in animals, preferably in mammals, more preferably in humans, preferably for cognitive enhancement, for the prophylaxis and/or treatment of disorders of the central nervous system, anxiety, panic disorders, depression, preferably bipolar disorders, cognitive memory disorders, senile dementia processes, neurodegenerative disorders, preferably Alzheimer's disease, Parkinson's disease, Huntington's disease and/or Multiple Sclerosis, schizophrenia, psychosis or infantile hyperkinesia (ADHD, attention deficit/hyperactivity disorder) and other disorders mediated by the 5-HT$_6$ serotonin receptor in humans and/or in animals, preferably in mammals, more preferably in humans.

Another aspect of the present invention is the use of at least one sulfonamide derivative of the previous general formula (Ic), optionally in the form of one of its stereoisomers, preferably enantiomers or diastereomers, its racemate, or in form of a mixture of at least two of its stereoisomers, preferably enantiomers or diastereomers, in any mixing ratio, or a corresponding physiologically acceptable salt thereof or a corresponding solvate thereof, for the manufacture of a medicament for 5-HT$_6$ receptor regulation, for the prophylaxis and/or treatment of a disorder or disease related to food intake, preferably for the regulation of appetite, for the maintenance, increase or reduction of body weight, for the prophylaxis and/or treatment of obesity, bulimia, anorexia, cachexia or type II diabetes (non insulin dependent diabetes mellitus), preferably type II diabetes caused by obesity, for the prophylaxis and/or treatment of gastrointestinal tract disorders, preferably irritable bowel syndrome, for cognitive enhancement, for the prophylaxis and/or treatment of disorders of the central nervous system, anxiety, panic disorders, depression, preferably bipolar disorders, cognitive memory disorders, senile dementia processes, neurodegenerative disorders, preferably Alzheimer's disease, Parkinson's disease, Huntington's disease and/or Multiple Sclerosis, schizophrenia, psychosis or infantile hyperkinesia (ADHD, attention deficit/hyperactivity disorder) and other disorders mediated by the 5-HT$_6$ serotonin receptor in humans and/or in animals, preferably in mammals, more preferably in humans.

The preparation of the corresponding pharmaceutical compositions as well as of the formulated medicaments may be carried out via conventional methods known in the prior art, for example, based on the indices of "Pharmaceutics: The Science of Dosage Forms", Second Edition, Aulton, M. E. (ED. Churchill Livingstone, Edinburgh (2002)); "Encyclopedia of Pharmaceutical Technology", Second Edition, Swarbrick, J. and Boylan, J. C. (Eds.), Marcel Dekker, Inc. New York (2002); "Modern Pharmaceutics", Fourth Edition, Banker G. S. and Rhodes C. T. (Eds.) Marcel Dekker, Inc. New York (2002), and "The Theory and Practice of Industrial Pharmacy", Lachman L., Lieberman H. and Kanig J. (Eds.), Lea & Febiger, Philadelphia (1986). The respective literature descriptions are incorporated as a reference and are part of this disclosure.

The pharmaceutical compositions, as well as the formulated medicaments prepared according to the present invention, may, in addition to at least one sulfonamide derivative of general formula (I), optionally in form of one of its stereoisomers, preferably enantiomers or diastereomers, its racemate, or in form of a mixture of at least two of its stereoisomers, preferably enantiomers or diastereomers, in any mixing ratio, or a corresponding physiologically acceptable salt or a corresponding solvate, comprise other conventional auxiliary substances known in the prior art, preferably excipients, fillers, solvents, diluents, dyes, coating agents, matrix forming agents and/or binders.

As the skilled persons in the art also knows, the choice of the auxiliary substances and the amounts thereof depend on the intended administration route, for example, rectal, intravenous, intraperitoneal, intramuscular, intranasal, oral, buccal or topical.

Medicaments suitable for oral administration are, for example, tablets, coated tablets, capsules or multiparticulates, preferably granules or pellets, optionally subjected to compression in tablets, filled in capsules or suspended in solutions, suspensions or suitable liquids.

Medicaments suitable for parenteral, topical or inhalatory administration may preferably be chosen from the group consisting of solutions, suspensions, quickly reconstitutable dry preparations and also sprays.

Medicaments suitable for oral or percutaneous use may release the sulfonamide compounds of general formula (I) in a sustained manner, the preparation of these sustained release medicaments generally being known in the prior art.

Suitable sustained release forms, as well as the materials and methods for the preparation thereof, are known in the art, for example from the indices of "Modified-Release Drug Delivery Technology", Rathbone, J. J I, Hadgraft, J. and Roberts, M. S. (Eds.), Marcel Dekker, Inc., New York (2002); "Handbook of Pharmaceutical Controlled Release Technology", Wise, D. L. (Ed.), Marcel Dekker, Inc. New York (2000); "Controlled Drug Delivery", Vol. I, Basic Concepts, Bruck, S. D. (Ed.), CRD Press, Inc., Boca Raton (1983), and by Takada, K. and Yoshikawa, H., "Oral Drug Delivery", Encyclopedia of Controlled Drug Delivery, Mathiowitz, E. (Ed.), John Wiley & Sons, Inc., New York (1999), Vol. 2, 728-742; Fix, J., "Oral Drug delivery, small intestine and colon", Encyclopedia of Controlled Drug Delivery, Mathiowitz, E. (Ed.), John Wiley & Sons, Inc., New York (1999), Vol. 2, 698-728. The respective literature references are incorporated by reference and form part of the disclosure.

The medicament of the present invention may also have at least one enteric coating, which dissolves according to the pH. As a result of this coating, the medicament may pass through the stomach without dissolving, and the compounds of general formula I are only released in the intestinal tract. The enteric coating preferably dissolves at a pH of between 5 and 7.5. The materials and methods suitable for preparing enteric coatings are also known in the prior art.

Typically, the pharmaceutical compositions and the medicaments comprise from 1 to 60% by weight of one or more sulfonamide derivatives of general formula (I), and from 40 to 99% by weight of one or more excipients.

The active substance amount to be administered to the patient varies according to the patient's weight, the administration route, the indication and the severity of the disorder. Usually from 1 mg to 2 g of at least one sulfonamide derivative of general formula (I) are administered per patient per day. The total daily dose may be administered to the patient in one or more doses.

Pharmaceutical Methods:

Binding to the 5HT$_6$ Serotonin Receptor

HEK-293 cell membranes expressing the recombinant human 5HT$_8$ receptor were supplied by Receptor Biology. The receptor concentration in said membranes is 2.18 pmol/mg of protein and the protein concentration is 9.17 mg/ml. The experimental protocol follows the method of B. L. Roth et al. [B. L. Roth, S. C. Craigo, M. S. Choudhary, A. Uluer, F. J. Monsma, Y. Shen, H. Y. Meltzer, D. R. Sibley: Binding of Typical and Atypical Antipshychotic Agents to 5-Hydroxytryptamine-6 and Hydroxytryptamine-7 Receptors. *The Journal of Pharmacology and Experimental Therapeutics*, 1994, 268, 1403], with slight modifications. The commercial membrane is diluted (1:40 dilution) with the binding buffer: 50 mM Tris-HCl, 10 mM MgCl$_2$, 0.5 mM EDTA (pH 7.4).

The radioligand used is [$^3$H]-LSD at a concentration of 2.7 nM, the final volume being 200 μl. Incubation begins by adding 100 μl of the membrane suspension (≈22.9 μg of membrane protein), and is prolonged for 60 minutes at a temperature of 37° C. Incubation ends by quick filtration in a Harvester Brandel Cell through fiberglass filters of the Schleicher & Schuell GF 3362 trademark, pretreated with a 0.5% polyethyleneimine solution. The filters are washed three times with three milliliters of 50 mM Tris HCl buffer, pH 7.4. The filters are transferred to vials and 5 ml of Ecoscint H. liquid scintillation cocktail are added to each vial. The vials are left to equilibrate for several hours prior to their counting in a 1414 Wallac Winspectral scintillation counter. The nonspecific binding is determined in the presence of 100 μM of serotonin. The assays are carried out in triplicate. The inhibition constants ($K_i$, nM) are calculated by non-linear regression analysis using the EBDA/LIGAND program [Munson and Rodbard, *Analytical Biochemistry*, 1980, 107, 220].

The respective literature descriptions are incorporated by reference and form part of the disclosure.

Measurements of Food Ingestion (Behavioural Model)

Male W rats (200-270 g) from Harlan, S. A. are used. The animals are acclimatized to the housings during at least 5 days prior to being subjected to any treatment. During this period, the animals are housed (in groups of five) in translucent cages and have free access to water and food. The animals are housed in individual cages at least 24 hours prior to starting the treatment.

The acute effect of the sulfonamide derivatives of formula (I) used inventively on food ingestion in rats in fasting conditions is then determined as follows:

The rats are kept in fasting conditions for 23 hours in their individual cages. After this period, the rats are orally or intraperitoneally treated with a dose of a composition containing a sulfonamide derivative of general formula (I) or a corresponding composition (vehicle) without said sulfonamide derivative. Immediately after this, the rat is left with preweighed food and the accumulated food intake is measured after 1, 2, 4 and 6 hours.

This food ingestion measuring method is also described in publications of Kask et al., *European Journal of Pharmacology* 414 (2001), 215-224, and Turnbull et al., *Diabetes*, Vol. 51, August, 2002. The respective bibliographic descriptions are incorporated as a reference and they form part of the disclosure.

The preparation of new compounds according to the invention is indicated in the following examples. The affinity for the 5HT$_6$ serotonin receptor, as well as the galenic formulas applicable to the compounds of the invention, is also described. The examples indicated below, given as an illustrative example, should in no way limit the scope of the invention.

EXAMPLES

Example 1

Preparation of N-[1-(2-dimethylaminoethyl)-1H-indole-7-yl]-naphtalene-1-sulfonamide 149.5 mg (0.66 mMol) of naphtalene-1-sulfonyl chloride were added to a solution of 122 mg (0.6 mMol) of 7-amino-3-(2-dimethylaminoethyl)-1H-indole in 2 ml of dimethylformamide and 116 mg of N-ethyldiisopropylamine. The reaction mixture was stirred at the room temperature for 20 hours. Then it was evaporated to dryness, slightly alkalinized with sodium bicarbonate solution and extracted with chloroform. The organic phase was repeatedly washed with water and saturated solution of sodium bicarbonate, it was separated and dried with anhydrous sodium sulfate. The organic solution was evaporated to dryness and the resulting solid was purified by chromatography, obtaining 120 mg (51%) of N-[1-(2-dimethylaminoethyl)-1H-indole-7-yl]-naphtalene-1-sulfonamide as a solid cream.

Example 2

Preparation of N-[1-(2-dimethylaminoethyl)-1H-indole-7-yl]-5-chloro-3-methyl-benzo[b]thiophene-2-sulfonamide 80 mg (30%) of the mentioned compound were obtained from 122 mg (0.6 mMol) of 7-amino-1-(2-dimethylaminoethyl)-1H-indole and 166 mg (0.66 mMol) of 5-chloro-3-methyl-benzo[b]thiophene-2-sulfonyl chloride, via the process described in the Example 1, as a yellowish solid.

Example 3

Preparation of N-[1-(2-dimethylaminoethyl)-1H-indole-7-yl]-4 phenylbenzenesulfonamide 27 mg (11%) of the mentioned compound were obtained from 122 mg (0.6 mMol) of 7-amino-1-(2-dimethylaminoethyl)-1H-indole and 167 mg (0.66 mMol) of 4-phenylbenzene sulfonyl chloride, via the process described in the Example 1, as a solid cream.

Example 4

Preparation of N-[1-(2-dimethylaminoethyl)-1H-indole-7-yl]-6-chloroimidazo[2,1-b]thiazole-5-sulfonamide 69 mg (27%) of the mentioned compound were obtained from 122 mg (0.6 mMol) of 7-amino-1-(2-dimethylaminoethyl)-1H-indole and 170 mg (0.66 mMol) of 6-chloroimidazo[2,1-b]thiazole-5-sulfonyl chloride, via the process described in the Example 1, as a solid cream.

Example 5

Preparation of 5-chloro-3-methyl-N-(1-(2-(pyrrolidinyl)ethyl)-1H-indol-7-yl)-benzo[b]thiophen-2-sulfonamide 146 mg (51%) of the mentioned compound were obtained from 137 mg (0.6 mMol) of 7-amino-1-(2-pyrrolidin-1-yl) ethyl)-1H-indole and 186 mg (0.66 mMol) of 5-chloro-3-methyl-benzo[b]thiophen-2-sulfonyl chloride via the process described in Example 1, as a solid.

Example 6

Preparation of N-(1-(2-(pyrrolidin-1-yl)ethyl)-1H-indol-7-yl)naphthalene-1-sulfonamide 120 mg (48%) of the mentioned compound were obtained from 137 mg (0.6 mMol) of 7-amino-1-(2-pyrrolidin-1-yl)

ethyl)-1H-indole and 150 mg (0.66 mMol) of naphthalene-1-sulfonyl chloride via the process described in Example 1, as a solid.

Example 7

Preparation of 6-chloro-N-(1-(2-(pyrrolidin-1-yl)ethyl)-1H-indol-7-yl)imidazo[2,1-b]thiazole-5-sulfonamide 100 mg (37%) of the mentioned compound were obtained from 137 mg (0.6 mMol) of 7-amino-1-(2-pyrrolidin-1-yl)ethyl)-1H-indole and 170 mg (0.66 mMol) 6-chloro-imidazo[2,1-b]thiazole-5-sulfonyl chloride via the process described in Example 1, as a solid.

Example 8

Preparation of 2-(naphth-1-yl)-N-(1-(2-(pyrrolidin-1-yl)ethyl)-1H-indol-7-yl)ethansulfonamide 130 mg (49%) of the mentioned compound were obtained from 137 mg (0.6 mMol) of 7-amino-1-(2-pyrrolidin-1-yl)ethyl)-1H-indole and 168 mg (0.66 mMol) of 2-(naphth-1-yl)ethansulfonyl chloride via the process described in Example 1, as a solid.

The yields are indicative and no added effort was made to improve them.

The melting point and spectroscopic data for identifying some of the compounds of the present invention are indicated in the following table.

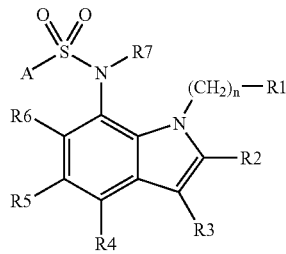

| Ex | $R_1$ | $R_2$ | $R_3$ | $R_4$ | $R_5$ | $R_6$ | $R_7$ | n | A | m.p. °C. | IR cm$^{-1}$ | $^1$H-NMR (300 MHz), δ (solvent) |
|---|---|---|---|---|---|---|---|---|---|---|---|---|
| 1 | (CH$_3$)$_2$N— | H | H | H | H | H | H | 2 | naphth-1-yl | 54-58 | 3422, 3057, 2943, 1489, 1315, 1158, 1132, 772, 581. | 2.42 (s, 6H); 2.89 (t, 2H, J=6.4 Hz); 4.88 (t, 2H, J=6.4 Hz); 6.17 (d, 1H, J=7.6 Hz); 6.44 (d, 1H, J=3.1 Hz); 6.60 (t, 1H, J=7.8 Hz); 7.16 (d, 1H, J=3.3 Hz); 7.32 (dd, 1H, J=7.9 Hz, J'=0.9 Hz); 7.53 (m, 1H); 7.63-7.67 (m, 2H); 8.04-8.09 (m, 2H); 8.17 (d, 1H, J=8.4 Hz); 8.75 (m, 1H). (CD$_3$OD) |
| 2 | (CH$_3$)$_2$N— | H | H | H | H | H | H | 2 | 5-chloro-2,3-dimethylbenzothien-6-yl | 57-65 | 3448, 2951, 1488, 1315, 1278, 1150, 1113, 1079, 861, 728, 648, 559. | 2.40 (s, 6H); 2.52 (s, 3H); 3.08 (t, 2H, J=5.7 Hz); 4.66 (t, 2H, J=5.7 Hz), 6.36 (d, 1H, 3.1 Hz); 6.70 (m, 2H); 7.15 (dd, 1H, J=7.0 Hz, J'=1.7 Hz); 7.24 (d, 1H, J=3.1 Hz); 7.49 (dd, 1H, J=8.6 Hz, J'=2.0 Hz); 7.91 (d, 1H, J=2.0 Hz); 8.00 (d, 1H, J=8.8 Hz). (DMSO-d6) |
| 3 | (CH$_3$)$_2$N— | H | H | H | H | H | H | 2 | biphenyl-4-yl | 137-140 | 2943, 1481, 1332, 1316, 1158, 1096, 764, 729, 668, 581. | 2.33 (s, 6H); 2.78 (m, 2H); 4.24 (m, 2H); 6.46 (d, 1H, J=3.1 Hz); 6.88 (d, 1H, J=3.1 Hz); 7.00 (t, 1H, J=7.8 Hz); 7.17 (d, 1H, J=7.5 Hz); 7.40-7.49 (m, 4H); 7.58 (m, 2H); 7.64 (AB sys, 2H, J=8.4 Hz); 7.86 (AB sys, 2H, J=8.4 Hz,). (CDCl$_3$). |
| 4 | (CH$_3$)$_2$N— | H | H | H | H | H | H | 2 | 6-chloroimidazo[2,1-b]thiazol-5-yl | 73-76 | 3448, 3110, 2928, 1485, 1459, 1316, 1270, 1238, 1182, 1124, 1091, 723, 622. | 2.66 (s, 6H); 3.28 (t, 2H, J=5.4 Hz); 4.74 (t, 2H); 6.30 (d, 1H, J=3.1 Hz); 6.64-6.70 (m, 2H); 7.01 (dd, 1H, J=6.5 Hz, J'=2.4 Hz); 7.19 (d, 1H, J=3.1 Hz); 7.45 (d, 1H, J=4.5 Hz); 7.89 (d, 1H, J=4.5 Hz). (DMSO-d6) |
| 5 | pyrrolidin-1-yl | H | H | H | H | H | H | 2 | 5-chloro-2,3-dimethylbenzothien-6-yl | 82-85 | | 1.87 (m, 4H); 2.41 (s, 3H); 3.02 (m, 4H); 3.34 (m, 2H); 4.70 (m, 2H); 6.34 (d, 1H, J=0.9 Hz); 6.62-6.80 (m, 2H); 7.09 (d, 1H, J=7.47 Hz); 7.21 (s, 1H); 7.46 (d, 1H, J=8.2 Hz); 7.87 (s, 1H); 7.97 (d, 1H, J=8.6 Hz). (DMSO-d6) |

-continued

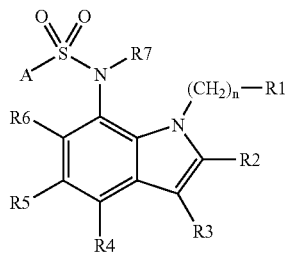

| Ex | R₁ | R₂ | R₃ | R₄ | R₅ | R₆ | R₇ | n | A | m.p. ° C. | IR cm⁻¹ | ¹H-NMR (300 MHz), δ (solvent) |
|---|---|---|---|---|---|---|---|---|---|---|---|---|
| 6 | pyrrolidinyl | H | H | H | H | H | H | 2 | 8-methylnaphthyl | 196-199 | | 1.79 (m, 4H); 2.79 (m, 4H); 3.18 (m, 2H); 4.66 (m, 2H); 6.30 (d, 1H, J=8.3 Hz); 6.35 (d, 1H, J=1.6 Hz); 6.60 (m, 1H); 7.14 (d, 1H, J=8.1 Hz); 7.25 (m, 1H); 7.56 (m, 1H); 7.60-7.74 (m, 2H); 8.05 (m, 2H); 8.16 (d, 1H, J=8.2 Hz); 8.79 (d, 1H, J=8.64 Hz). (DMSO-d6) |
| 7 | pyrrolidinyl | H | H | H | H | H | H | 2 | 6-chloro-5-methylimidazo[2,1-b]thiazole | 92-95 | | 1.84 (m, 2H); 1.98 (m, 2H); 3.04 (m, 2H); 3.58 (m, 4H); 4.87 (t, 2H, J=6.7 Hz); 6.15 (d, 1H, J=7.8 Hz); 6.49 (d, 1H, J=2.6 Hz); 6.73 (t, 1H, J=7.6 Hz); 7.33-7.43 (m, 3H, J=5.3 Hz); 7.46 (d, 1H, J=7.9 Hz); 9.83 (bs, 1H); 10.32 (s, 1H). (DMSO-d6 + TFA) |
| 8 | pyrrolidinyl | H | H | H | H | H | H | 2 | 1-(2-naphthyl)ethyl | 46-49 | | 1.69 (m, 4H); 2.59 (m, 4H); 2.90 (m, 2H); 3.53 (m, 4H); 4.65 (t, 2H, J=6.2 Hz); 6.45 (d, 1H, J=3.1 Hz); 6.94 (t, 1H, J=7.6 Hz); 7.05 (m, 1H); 7.35 (d, 1H, J=3.1 Hz); 7.39-7.56 (m, 5H); 7.83 (d, 1H, J=7.6 Hz); 7.94 (m, 2H). (DMSO-d6) |

The daily posology in human medicine is comprised between 1 milligram and 2 grams of medicinal product which may be administered in one or several doses. The compositions are prepared under forms that are compatible with the administration route used, preferably tablets, coated tablets, capsules, suppositories, solutions or suspensions. These compositions are prepared via known methods and comprise from 1 to 60% by weight of the medicament substance (compound of general formula I), and 40 to 99% by weight of the suitable pharmaceutical vehicle compatible with the active substance and the physical form of the composition used.

The formula of a tablet containing a product of the invention is provided by way of example:

Example of Formula Per Tablet:

| | |
|---|---|
| Example 1 | 5 mg |
| Lactose | 60 mg |
| Crystalline cellulose | 25 mg |
| Povidone K 90 | 5 mg |
| Pregelatinized starch | 3 mg |
| Colloidal silicon dioxide | 1 mg |
| Magnesium stearate | 1 mg |
| Total weight per tablet | 100 mg |

The invention claimed is:

1. A sulfonamide compound of general formula (Ia),

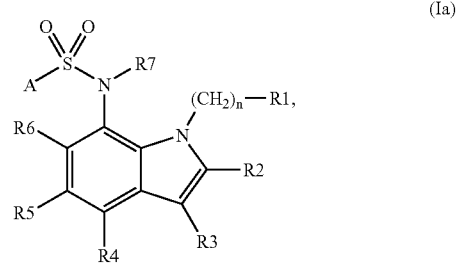

wherein
$R^1$ is a $-NR^8 R^9$ radical or a saturated or unsaturated, optionally at least mono-substituted cycloaliphatic radical, which may optionally contain at least one heteroatom as a ring member and which may be condensed with a saturated or unsaturated, optionally at least mono-substituted mono- or bicyclic cycloaliphatic ring system which may optionally contain at least one heteroatom as a ring member, $R^2, R^3, R^4, R^5$ and $R^6$, identical or different, each represent hydrogen, halogen, nitro, alkoxy, cyano, a saturated or unsaturated, linear or branched, optionally at least mono-substituted aliphatic radical, or an optionally at least mono-substituted phenyl radical or an optionally at least mono-substituted heteroaryl radical, $R^7$ represents hydrogen or a saturated or unsaturated, linear or branched, optionally at least mono-substituted aliphatic radical, $R^8$ $R^9$, identical or different, represent hydrogen or a saturated or unsaturated, linear or branched, optionally at least mono-substituted aliphatic radical, with the proviso that $R^8$ and $R^9$ are not hydrogen at the same time, and if one of them, $R^8$ or $R^9$, is a saturated or unsaturated, linear or branched, optionally at least mono-substituted $C_1$-$C_4$ aliphatic radical, the other one is a saturated or unsaturated, linear or branched, optionally at least mono-substituted aliphatic radical with at least five carbon atoms, or $R^8$ $R^9$ together with the bridging nitrogen atom form a saturated or unsaturated, optionally at least mono-substituted heterocyclic ring, which may contain at least one additional heteroatom as a ring member and/or which may be condensed with a saturated or unsaturated, optionally at least mono-substituted mono- or bicyclic cycloaliphatic ring system, which may optionally contain at least one heteroatom as a ring member, A represents an optionally at least mono-substituted mono- or polycyclic aromatic ring system, which may be bonded via an optionally at least mono-substituted alkylene, alkenylene or alkynylene group and/or which may contain at least one heteroatom as a ring member in one or more of its rings, n is 0, 1, 2, 3 or 4;

optionally in form of one of its stereoisomers, its racemate or in form of a mixture of at least two of its stereoisomers, in any mixing ratio, or a salt thereof.

2. A compound according to claim 1, wherein $R^1$ represents a —$NR^8R^9$ radical or a saturated or unsaturated, optionally at least mono-substituted 5- or 6-membered cycloaliphatic radical which may optionally contain at least one heteroatom as a ring member and/or which may be condensed with a saturated or unsaturated, optionally at least mono-substituted mono- or bicyclic cycloaliphatic ring system, which may optionally contain at least one heteroatom as a ring member, whereby the rings of the ring system are 5- or 6-membered.

3. A compound according to claim 1 or 2, characterized in that $R^2$, $R^3$, $R^4$, $R^5$ and $R^6$, identical or different, each represent hydrogen, a linear or branched, optionally at least mono-substituted $C_1$-$C_6$ alkyl radical, a linear or branched, optionally at least mono-substituted $C_2$-$C_6$ alkenyl radical or a linear or branched, optionally at least mono-substituted $C_2$-$C_6$ alkynyl radical.

4. A compound according to claim 1, wherein $R^7$ represents hydrogen, a linear or branched, optionally at least mono-substituted $C_1$-$C_6$ alkyl radical, a linear or branched, optionally at least mono-substituted $C_2$-$C_6$ alkenyl radical or a linear or branched, optionally at least mono-substituted $C_2$-$C_6$ alkynyl radical.

5. A compound according to claim 1, wherein $R^8$ and $R^9$, identical or different, each represent hydrogen, a linear or branched, optionally at least mono-substituted $C_1$-$C_{10}$ alkyl radical, a linear or branched, optionally at least mono-substituted $C_2$-$C_{10}$ alkenyl radical or a linear or branched, optionally at least mono-substituted $C_2$-$C_{10}$ alkynyl radical, or $R^8$ and $R^9$ together with the bridging nitrogen atom form a saturated or unsaturated, optionally at least mono-substituted 5 - or 6-membered heterocycle ring, which may contain at least one additional heteroatom as a ring member and/or which may be condensed with a saturated or unsaturated, optionally at least mono-substituted mono- or bicyclic cycloaliphatic ring system, which may optionally contain at least one heteroatom as a ring member, whereby the rings of the ring system are 5-6- or 7-membered.

6. A compound according to claim 5, wherein $R^8$ and $R^9$, identical or different, each represent hydrogen or a linear or branched $C_1$-$C_{10}$ alkyl radical, or $R^8$ and $R^9$, together with the bridging nitrogen atom form a radical chosen from the group consisting of

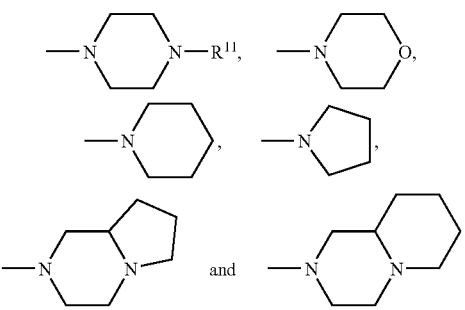

wherein $R^{11}$, if present, represents hydrogen, a linear or branched $C_1$-$C_6$ alkyl radical or a benzyl radical.

7. A compound according to claim 1, wherein A represents an optionally at least mono-substituted mono- or polycyclic aromatic ring system, wherein the ring(s) is/are 5- or 6-membered, which may be bonded via an optionally at least mono-substituted $C_1$-$C_6$ alkylene group, an optionally at least mono-substituted $C_2$-$C_6$ alkenylene group or an optionally at least mono-substituted $C_2$-$C_6$ alkynylene group and/or wherein the ring(s) may contain at least one heteroatom as a ring member

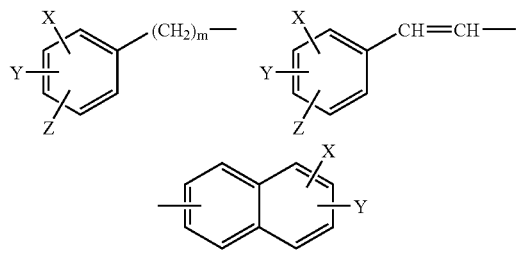

8. A compound of general formula (Ia) according to claim 1 selected from the group consisting of

[5]   5-chloro-3-methyl-N-(1-(2-(pyrrolidin-1-yl)ethyl)-1H-indol-7-yl)-benzo [b]thiophen-2-sulfonamide,

[6]   N-(1-(2-(pyrrolidin-1-yl)ethyl)1-H-indol-7-yl)naphthalene-1-sulfonamide,

[7]   6-chloro-N-(1-(2-(pyrroldin-1-yl)ethyl)-1H-indol-7-yl)imidazo[2,1-b]thiazole-5-sulfonamide,

[8]   2-(naphth 1-yl)-N-(1-(2-(pyrrolidin-1-yl)ethyl)-1-H-indol-7-yl)ethansulfonamide, and their corresponding salts.

9. A sulfonamide compound of general formula (Ib),

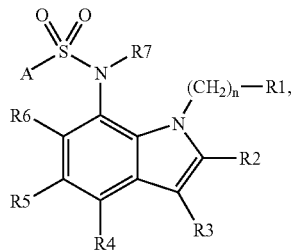

wherein
$R^1$ represents a —$NR^8R^9$ radical,
$R^2$, $R^3$, $R^4$, $R^5$ and $R^6$, identical or different, each represent hydrogen, halogen, nitro, alkoxy, cyano, a saturated or unsaturated, linear or branched, optionally at least mono-subtituted aliphatic radical, or an optionally at least mono-substituted phenyl radical or an optionally at least mono-substituted heteroaryl radical,
$R^7$ represents hydrogen or a saturated or unsaturated, linear or branched, optionally at least mono-substituted aliphatic radical,
$R^8$ and $R^9$, identical or different, represent hydrogen or a saturated or unsaturated, linear or branched, optionally at least mono-substituted $C_{1-4}$ aliphatic radical,
A represents an optionally at least mono-substituted mono- or polycyclic aromatic ring system, which may be bonded via an optionally at least mono-substituted alkylene, alkenylene or alkynylene group and/or which may contain at least one heteroatom as a ring member in one or more of its rings,
n is 0, 1, 2, 3 or 4;
optionally in form of one of its stereoisomers, its racemate or in form of a mixture of at least two of its stereoisomers, in any mixing ratio, or a salt thereof.

10. A compound according to claim 9, wherein $R^2$, $R^3$, $R^4$, $R^5$ $R^6$, identical or different, each represent hydrogen, a linear or branched, optionally at least mono-substituted $C_1$-$C_6$ alkyl radical, a linear or branched, optionally at least mono-substituted $C_2$-$C_6$ alkenyl radical or a linear or branched, optionally at least mono-substituted $C_2$-$C_6$ alkynyl radical.

11. A compound according to claim 9, wherein $R^7$ represents hydrogen, a linear or branched, optionally at least mono-substituted $C_1$-$C_6$ alkyl radical, a linear or branched, optionally at least mono-substituted $C_2$-$C_6$ alkenyl radical or a linear or branched, optionally at least mono-substituted $C_2$-$C_6$ alkynyl radical.

12. A compound according to claim 9, wherein $R^8$ and $R^9$, identical or different, each represent hydrogen or a linear or branched, optionally at least mono-substituted $C_1$-$C_4$ alkyl radical,
with the proviso that $R^8$ and $R^9$ are not hydrogen at the same time.

13. A compound according to claim 9, wherein A represents an optionally at least mono-substituted mono- or polycyclic aromatic ring system, wherein the ring(s) is/are 5- or 6-membered, which may be bonded via an optionally at least mono-substituted $C_1$-$C_6$ alkylene group, an optionally at least mono-substituted $C_2$-$C_6$ alkenylene group or an optionally at least mono-substituted $C_2$-$C_6$ alkynylene group and/or wherein the ring(s) may contain at least one heteroatom as a ring member.

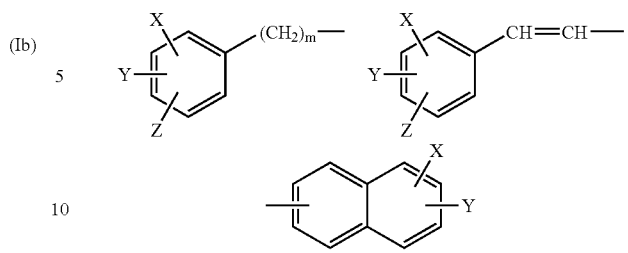

14. A compound according to claim 9 selected from the group consisting of
[1] N-[1-(2-dimethylaminoethyl)-1H-indole-7-yl]-naphtalene-1-sulfonamide,
[2] N-[1-(2-dimethylaminoethyl)-1H-indole-7-yl]-5-chloro-3-methylbenzo[b]thiophene-2-sulfonamide,
[3] N-[1-(2-dimethylaminoethyl)-1H-indole-7-yl]-4-phenylbenzenesulfonamide,
[4] N-[1-(2-dimethylaminoethyl)-1H-indole-7-yl]-6-chloroimidazo[2,1-]thiazole-5-sulfonamide,
and their corresponding salts.

15. A process for obtaining a sulfonamide derivative of general formula (Ia), according to claim 1, wherein at least one compound of general formula (II), or one of its suitably protected derivatives,

wherein X is an acceptable leaving group, and is reacted with at least one 7-aminoindole of general formula (III), or one of its suitably protected derivatives;

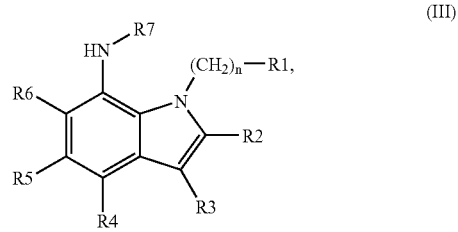

to obtain the corresponding sulfonamide and optionally, from the latter, the protective groups may be removed if necessary.

16. A process for obtaining a sulfonamide derivative of general formula (Ia), according to claim 1, wherein $R^7$ is a linear or branched $C_1$-$C_6$ alkyl, comprising reacting at least one compound of general formula (Ia) wherein $R^7$ is an hydrogen atom, with an alkyl halogenide or dialkyl sulfate.

17. A process for preparing a salt of general formula (Ia) according to claim 1, wherein at least one compound of the general formula (Ia) is reacted with a mineral acid or organic acid in a suitable solvent.

18. A pharmaceutical composition comprising a therapeutically effective amount of at least one compound according to claim 1 and optionally one or more pharmacologically acceptable excipients.

19. A pharmaceutical composition comprising a therapeutically effective amount of at least one compound according to claim 9 and optionally one or more pharmacologically acceptable excipients.

20. The compound according to claim 1, wherein the compound is in the form of a physiologically acceptable salt thereof.

21. The compound according to claim 1, wherein the compound is in the form of its enantiomers or diastereomers or in the form or a mixture of at least two of its enantiomers and/or diastereomers.

22. The compound according to claim 2 wherein $R^1$ represents an —$NR^8R^9$ radical or a radical chosen from the group consisting of

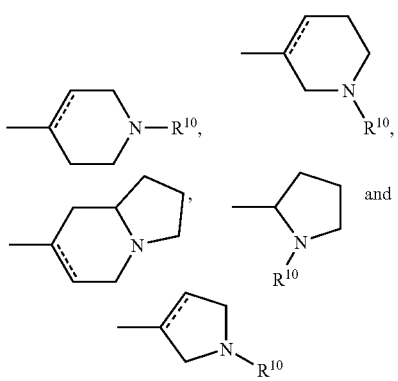

wherein, if present, the dotted line is an optional chemical bond, and $R^{10}$ is hydrogen, a linear or branched $C_1$-$C_6$ alkyl radical or a benzyl radical.

23. The compound according to claim 22, wherein $R^{10}$ is hydrogen or a $C_1$-$C_2$ alkyl radical.

24. The compound according to claim 3, wherein $R^2$, $R^3$, $R^4$, $R^5$ and $R^6$, identical or different, each represent hydrogen or a linear or branched, optionally at least mono substituted, $C_1$-$C_6$ alkyl radical.

25. The compound according to claim 24, wherein $R^2$, $R^3$, $R^4$, $R^5$ and $R^6$ each represent hydrogen.

26. The compound according to claim 4, wherein $R^7$ represents hydrogen or a linear or branched, optionally at least mono substituted $C_1$-$C_6$ alkyl radical.

27. The compound according to claim 26, wherein $R^7$ represents hydrogen or a $C_1$-$C_2$ alkyl radical.

28. The compound according to claim 6, wherein $R^{11}$ represents hydrogen or a $C_1$-$C_2$ alkyl radical.

29. The compound according to claim 7, wherein A represents an optionally at least mono-substituted mono- or polycyclic aromatic ring system, wherein the ring(s) is/are 5-or 6-membered and wherein one or more of the rings contain at least one heteroatom, or a radical chosen from the group consisting of

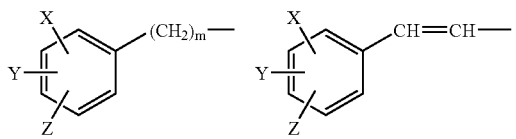

-continued

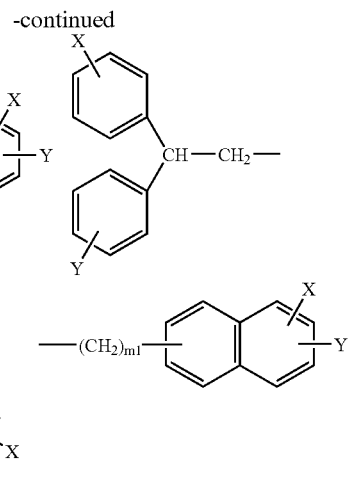

wherein X, Y, Z, independently from one another, each represent a radical selected from the group consisting of hydrogen, fluorine, chlorine, bromine, linear or branched $C_1$-$C_6$ alkyl, linear or branched $C_1$-$C_6$ alkoxy, linear or branched $C_1$-$C_6$ alkylthio, a trifluoromethyl radical, a cyano radical and a —$NR^{12}R^{13}$ radical, wherein $R^{12}$ $R^{13}$, identical or different, each represent hydrogen or linear or branched $C_1$-$C_6$ alkyl, W represents a single chemical bond between the two rings, a $CH_2$, O, S group or a $NR^{14}$ radical, wherein $R^{14}$ is hydrogen or a linear or branched $C_1$-$C_6$ alkyl, m is 0, 1, 2, 3 or 4 and m1 is 1 or 2.

30. The compound according to claim 9, wherein the salt is in the form of a physiologically acceptable salt thereof.

31. The compound according to claim 9, wherein the compound is in the form of its enantiomers or diastereomers, or in the form of a mixture of at least two of its enantiomers and/or diastereomers.

32. The compound according to claim 10, wherein $R^2$, $R^3$, $R^4$, $R^5$ and $R^6$, identical or different, each represent hydrogen or a linear or branched, optionally at least mono substituted, $C_1$-$C_6$ alkyl radical.

33. The compound according to claim 32, wherein $R^2$, $R^3$, $R^4$, $R^5$ and $R^6$ each represent hydrogen.

34. The compound according to claim 11, wherein $R^7$ represents hydrogen or a linear or branched, optionally at least mono-substituted $C_1$-$C_6$ alkyl radical.

35. The compound according to claim 34, wherein $R^7$ represents hydrogen or a $C_1$-$C_2$ alkyl radical.

36. The compound according to claim 12, wherein $R^8$ $R^9$, identical or different, each represent hydrogen or $C_1$-$C_2$ alkyl radical, with the proviso that $R^8$ and $R^9$ are not hydrogen at the same time.

37. The compound according to claim 13, wherein A represents an optionally at least mono-substituted mono- or polycyclic aromatic ring system, wherein the ring(s) is/are 5- or 6-membered and wherein one or more of the rings contain at least one heteroatom, or a radical chosen from the group consisting of

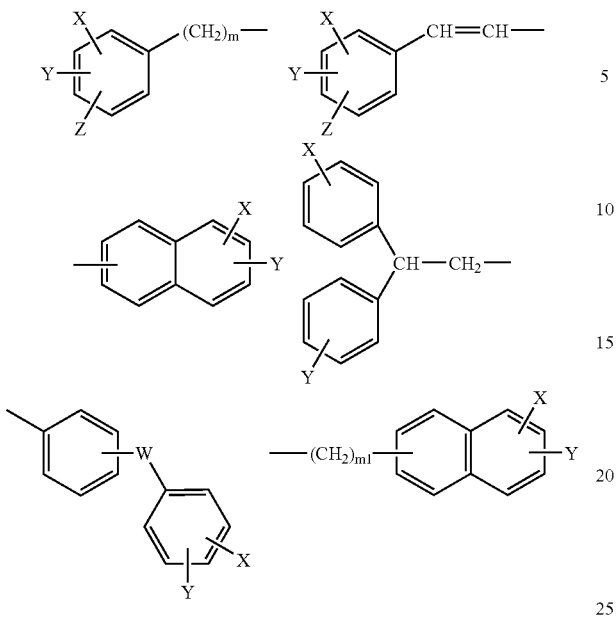

wherein X, Y, Z, independently from one another, each represent a radical selected from the group consisting of hydrogen, fluorine, chlorine, bromine, linear or branched $C_1$-$C_6$ alkyl, linear or branched $C_1$-$C_6$ alkoxy, linear or branched $C_1$-$C_6$ alkylthio, a trifluoromethyl radical, a cyano radical and a —$NR^{12}R^{13}$ radical, wherein $R^{12}$ and $R^{13}$, identical or different, each represent hydrogen or linear or branched $C_1$-$C_6$ alkyl, W represents a single chemical bond between the two rings, a $CH_2$, O, S group or a $NR^{14}$ radical, wherein $R^{14}$ is hydrogen or a linear or branched $C_1$-$C_6$ alkyl, m is 0, 1, 2, 3, or 4 and m1 is 1 or 2.

38. A process for obtaining a sulfonamide derivative of general formula (Ib) as defined in claim 9, wherein at least one compound of general formula (II), or one of its suitably protected derivatives,

wherein X is an acceptable leaving group, is reacted with at least one 7-aminoindole of general formula (III), or one of its suitably protected derivatives;

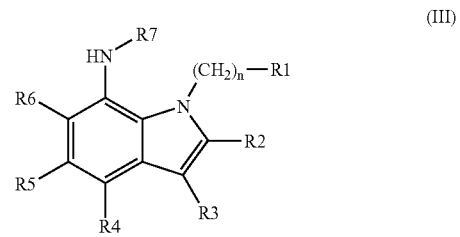

to obtain the corresponding sulfonamide and optionally, from the latter, the protective groups may be removed if necessary.

39. A process for obtaining a sulfonamide derivative of general formula (Ib) as defined in claim 9, wherein $R^7$ is a linear or branched $C_1$-$C_6$ alkyl comprising reacting at least one compound of general formula (Ib), wherein $R^7$ is a hydrogen atom, with an alkyl halogenide or dialkyl sulfate.

40. A process for preparing a salt of general formula (Ib), as defined in claim 9, wherein at least one compound of the general formula (Ib) is reacted with a mineral acid or organic acid in a suitable solvent.

41. The process according to claim 15, wherein X is a halogen atom.

42. The process according to claim 15, wherein X is chlorine.

43. The process according to claim 38, wherein X is a halogen atom.

44. The process according to claim 38, wherein X is chlorine.

* * * * *

UNITED STATES PATENT AND TRADEMARK OFFICE
CERTIFICATE OF CORRECTION

| | | |
|---|---|---|
| PATENT NO. | : 7,414,070 B2 | Page 1 of 1 |
| APPLICATION NO. | : 10/566403 | |
| DATED | : August 19, 2008 | |
| INVENTOR(S) | : Merce Vidal et al. | |

It is certified that error appears in the above-identified patent and that said Letters Patent is hereby corrected as shown below:

On the title page, Item (86), the PCT should read:

-- (86) PCT No.: PCT/EP2004/008513
§ 371 (c)(1),
(2), (4) Date: Aug. 11, 2006 --

Signed and Sealed this

Seventh Day of October, 2008

JON W. DUDAS
*Director of the United States Patent and Trademark Office*